United States Patent
Ghazi et al.

(10) Patent No.: US 10,799,193 B2
(45) Date of Patent: Oct. 13, 2020

(54) METHOD AND APPARATUS FOR ANATOMICALLY-SPECIFIED CONFORMATION COMPUTED TOMOGRAPHY

(71) Applicant: Malcova LLC, Baltimore, MD (US)

(72) Inventors: Peymon Mirsaeid Ghazi, Baltimore, MD (US); Tara Renee Ghazi, Baltimore, MD (US)

(73) Assignee: MALCOVA LLC, Baltimore, MD (US)

( * ) Notice: Subject to any disclaimer, the term of this patent is extended or adjusted under 35 U.S.C. 154(b) by 0 days.

(21) Appl. No.: 16/557,321

(22) Filed: Aug. 30, 2019

(65) Prior Publication Data

US 2020/0253567 A1 Aug. 13, 2020

Related U.S. Application Data

(60) Provisional application No. 62/804,693, filed on Feb. 12, 2019.

(51) Int. Cl.
*A61B 6/03* (2006.01)
*A61B 6/02* (2006.01)
(Continued)

(52) U.S. Cl.
CPC .............. *A61B 6/032* (2013.01); *A61B 6/027* (2013.01); *A61B 6/06* (2013.01); *A61B 6/4458* (2013.01); *A61B 6/502* (2013.01); *A61B 6/54* (2013.01)

(58) Field of Classification Search
CPC ........... A61B 6/032; A61B 6/027; A61B 6/06; A61B 6/4458; A61B 6/502; A61B 6/54
See application file for complete search history.

(56) References Cited

U.S. PATENT DOCUMENTS

| 4,145,610 A | 3/1979 | Perilhou |
| 4,196,352 A * | 4/1980 | Berninger .............. A61B 6/032 378/10 |

(Continued)

FOREIGN PATENT DOCUMENTS

| JP | H0638957 A | 2/1994 |
| WO | WO-2014058775 A1 | 4/2014 |

(Continued)

OTHER PUBLICATIONS

Co-pending U.S. Appl. No. 16/537,283, filed Aug. 9, 2019.
PCT/US2020/017760 International Search Report and Written Opinion dated May 4, 2020.

*Primary Examiner* — Bo Joseph Peng
(74) *Attorney, Agent, or Firm* — Wilson Sonsini Goodrich & Rosati

(57) ABSTRACT

Described are anatomically specified conformation computed tomography (ASC-CT) systems, which are fully tomographic x-ray imaging systems configured to conform to the contour of the anatomy of interest and perform a near scatter-free image acquisition, thereby providing an enhanced contrast resolution in the reconstructed CT image volume. The apparatus comprises independently controlled, yet synchronized, x-ray generation and detection assemblies configured to perform a tomographic image acquisition. The method of image acquisition entails adjusting the layout of the x-ray panels within the detector assembly based on the shape of the anatomy, followed by capturing a collimated, narrow x-ray beam composed of primary photons while sweeping a circular trajectory around the anatomy placed in the field of view, resulting in a conforming sinogram of the anatomy.

20 Claims, 21 Drawing Sheets

(51) Int. Cl.
*A61B 6/00* (2006.01)
*A61B 6/06* (2006.01)

(56) References Cited

U.S. PATENT DOCUMENTS

| | | |
|---|---|---|
| 4,315,146 A | 2/1982 | Rudin |
| 4,975,933 A | 12/1990 | Hampel |
| 5,966,422 A | 10/1999 | Dafni et al. |
| 6,438,210 B1 | 8/2002 | Castleberry |
| 6,744,852 B2 | 6/2004 | Klotz et al. |
| 6,990,171 B2 | 1/2006 | Toth et al. |
| 7,088,799 B2 | 8/2006 | Hoffman |
| 8,199,883 B2 | 6/2012 | Arenson et al. |
| 8,325,879 B2 | 12/2012 | Loos et al. |
| 9,208,918 B2 | 12/2015 | Tybinkowski et al. |
| 9,392,984 B2 | 7/2016 | Pelc et al. |
| 2004/0013225 A1* | 1/2004 | Gregerson ............. A61B 6/032 378/19 |
| 2005/0013411 A1 | 1/2005 | Yahata et al. |
| 2013/0235973 A1* | 9/2013 | Murakoshi ........... A61B 6/4233 378/37 |
| 2014/0098930 A1* | 4/2014 | Litzenberger ........ A61B 6/0492 378/4 |
| 2015/0279496 A1 | 10/2015 | Bauer |
| 2016/0035450 A1 | 2/2016 | Date et al. |
| 2016/0361036 A1* | 12/2016 | Ray ....................... A61B 6/508 |
| 2018/0289348 A1* | 10/2018 | Cox ....................... A61B 6/508 |
| 2018/0317867 A1 | 11/2018 | Boone et al. |

FOREIGN PATENT DOCUMENTS

| | | | |
|---|---|---|---|
| WO | WO-2016126829 A1 | 8/2016 | |
| WO | WO-2017073996 A1 * | 5/2017 | ........... A61B 6/4435 |

\* cited by examiner

METHOD AND APPARATUS FOR ANATOMICALLY-SPECIFIED CONFORMATION COMPUTED TOMOGRAPHY

CROSS-REFERENCE TO RELATED APPLICATIONS

This application claims the benefit of U.S. Provisional Application No. 62/804,693, filed Feb. 12, 2019, which is hereby incorporated by reference in its entirety.

BACKGROUND OF THE INVENTION

Radiologic computed tomography (CT) is a modality of imaging the internal areas of the human body using x-ray equipment, special image acquisition techniques and image reconstruction methods. A class of CT systems—dedicated CT systems—is designed to scan a specific anatomy such as the extremities, the head, and the female breast.

TECHNICAL FIELD

The present invention relates to an apparatus and methods for x-ray computed tomography of an anatomy.

SUMMARY OF THE INVENTION

Traditional image acquisition methodologies such as fan-beam CT, cone beam CT and helical CT have been used in the design of dedicated CT systems. The primary goal of CT technologies is to provide high quality images; however, they suffer from image degradations caused by several artifacts. Most notable, as it relates to this invention, are the image artifacts that stem from 1) scattered radiation and 2) the acquisition of sub-normal incident rays on detector elements, both of which result from wide beam image acquisition modes.

The minimum physical structure of a CT system in general consists of one or multiple sources of generating x-ray photons (x-ray generation unit), one or more x-ray detection units and a mechanism of rotation around the body that enables collection of projections. The precise locations of generating and detecting an x-ray beam are required for a successful 3D image reconstruction. Therefore, the traditional design of a CT system has incorporated x-ray generation and detection units that are 1) mechanically attached to a single rigid gantry, and 2) locked in a fixed position relative to one another. The classic gantry-based design requires the employment of large x-ray detection units in order to cover the entire volume of the anatomy. The result of this classic collection method is that a significant amount of unwanted scattered photons, large fan angle, and/or cone angle incident photons are collected along with the wanted photons that comprise the signal.

X-ray scattering in CT is a well-studied subject. It is generally known that the acquisition of scattered photons leads to severe degradation of the image quality by reducing contrast, generating streak and shading artifacts and miscalibration of Hounsfield unit (HU) values. Strategies for scatter management in CT include increasing the anatomy-to-detector gap or limiting the field of view (FOV), use of an antiscatter grid and algorithmic methodologies; however, each strategy entails inherent or practical limitations and may be capable of affecting only a portion of the frequency response of the imaging system to scattered radiation. For instance, enlarging the gap or reducing the FOV is technically impractical for many applications and causes degradation in spatial resolution. The dose penalty associated with utilization of antiscatter grid technology is a prohibitive fact limiting its use in clinical radiology. Scattered radiation has a negative impact throughout the reconstructed image volume's frequency spectrum. Algorithmic correction techniques attempt to reduce only the low-frequency impacts of the x-ray scatter. High-frequency impacts of the x-ray scatter, such as reduced contrast of small microcalcifications in the reconstructed image, is almost an impossible task as the recorded primary and scattered photons in the projections are indifferentiable.

Clinical studies and health diagnostics in the medical field are heavily dependent on the quality and accuracy of CT images. The ability to reliably detect microcalcifications—strong indicators of breast cancer—within these images is of particular important. The ASC-CT design specifically addresses and resolves the two classes of artifacts discussed above, with the end result of producing higher quality images that are far less contaminated by artifacts.

The present subject matter relates to an apparatus and method for tomographic x-ray imaging of a body part. An objective of the disclosure is to present the design of a CT scanner system that results in images uncontaminated by artifacts resulting from scattered radiation and/or the detection of sub-orthogonal incident rays.

The apparatus is composed of x-ray production and detection assemblies installed on separate physical and structural platforms, which rotate independently, but in synchrony, around the anatomy. A method of scanning entails synchronized rotational motion of the x-ray generation and detection assemblies as x-rays are emitted and detected. The detection assembly is composed of Time-delayed-integration (TDI) enabled line detectors. The x-ray beam emitted from the generation assembly is collimated such that the anatomy is exposed only to those projections on a trajectory to be received by the sensitive areas of the detection assembly are passed. The rotational trajectory and internal structure of the detection assembly is constrained to conform to the contour of the anatomy positioned in the field of view (FOV). The result is exposing the anatomy to a collimated narrow x-ray beam sweeping the anatomy's entire volume and capturing only the primary x-ray photons incident perpendicularly on the sensing areas of the detection assembly.

In one aspect, disclosed herein are radiologic computed tomography (CT) systems comprising: a x-ray generation assembly affixed to a first rotational robotic platform, the x-ray generation assembly configured to generate a collimated beam of x-ray photons; a x-ray detection assembly affixed to a second rotational robotic platform, the x-ray detection assembly comprising at least one line detector configured to detect the beam of x-ray photons; and a controller, configured to control the first rotational robotic platform to rotate the x-ray generation assembly on a first trajectory and to control the second rotational robotic platform to rotate the x-ray detection assembly on a second trajectory, the first rotational robotic platform and the second rotational robotic platform rotating independently and in synchrony in conformity to a shape of a target to capture primary x-ray photons substantially perpendicularly incident on the at least one line detector of the x-ray detection assembly. In some embodiments, the x-ray detection assembly comprises a plurality of line detectors. In further embodiments, each line detector is independently positioned at a cone angle. In further embodiments, each line detector is independently positioned at a tilt angle. In further embodiments, each line detector is independently positioned at a distance from a focal spot of a x-ray source of the x-ray generation assembly. In some embodiments, captured scattered radiation is constrained to photons scattered less than 20 degrees from a primary path. In some embodiments, x-ray photons captured by the x-ray detection assembly are limited to x-ray photons within 20 degrees from orthogonal. In some embodiments, the target is an anatomical target. In various further embodiments, the beam has a x-ray beam energy falling within a diagnostic range of 20 keV to 140 keV. In some embodiments, the anatomical target is a human extremity. In further embodiments, the beam has a beam energy of about 50 keV. In some embodiments, the anatomical target is a human female breast. In further embodiments, the beam has a beam energy of about 25 keV. In some embodiments, the anatomical target is a whole human body. In some embodiments, the beam has a fan angle less than 2 degrees. In some embodiments, the first trajectory conforms to the shape of the target. In some embodiments, the first trajectory is an elliptical trajectory. In further embodiments, the elliptical trajectory is a helical trajectory or a spiral trajectory. In some embodiments, the first trajectory is a circular trajectory. In further embodiments, the circular trajectory is a helical trajectory or a spiral trajectory. In some embodiments, the second trajectory conforms to the shape of the target. In some embodiments, the second trajectory is an elliptical trajectory. In further embodiments, the elliptical trajectory is a helical trajectory or a spiral trajectory. In some embodiments, the second trajectory is a circular trajectory. In further embodiments, the circular trajectory is a helical trajectory or a spiral trajectory.

In another aspect, disclosed herein are computer-implemented methods of performing radiologic computed tomography (CT) comprising: generating, by a x-ray generation assembly affixed to a first rotational robotic platform, a collimated beam of x-ray photons; detecting, by a x-ray detection assembly affixed to a second rotational robotic platform and comprising at least one line detector, the beam of x-ray photons; and controlling, by a controller unit, the first rotational robotic platform to rotate the x-ray generation assembly on a first trajectory and to control the second rotational robotic platform to rotate the x-ray detection assembly on a second trajectory, the first rotational robotic platform and the second rotational robotic platform rotating independently and in synchrony in conformity to a shape of a target to capture primary x-ray photons substantially perpendicularly incident on the at least one line detector of the x-ray detection assembly. In some embodiments, the x-ray detection assembly comprises a plurality of line detectors. In further embodiments, the method comprises independently positioning each line detector at a cone angle. In further embodiments, the method comprises independently positioning each line detector at a tilt angle. In further embodiments, the method comprises independently positioning each line detector at a distance from a focal spot of a x-ray source of the x-ray generation assembly. In some embodiments, captured scattered radiation is constrained to photons scattered less than 20 degrees from a primary path. In some embodiments, x-ray photons captured by the x-ray detection assembly are limited to x-ray photons within 20 degrees from orthogonal. In some embodiments, the target is an anatomical target. In various further embodiments, the beam has a x-ray beam energy falling within a diagnostic range of 20 keV to 140 keV. In some embodiments, the anatomical target is a human extremity. In further embodiments, the beam has a beam energy of about 50 keV. In some embodiments, the anatomical target is a human female breast. In further embodiments, the beam has a beam energy of about 25 keV. In some embodiments, the anatomical target is a whole human body. In some embodiments, the beam has a fan angle less than 2 degrees. In some embodiments, the first trajectory conforms to the shape of the target. In some embodiments, the first trajectory is an elliptical trajectory. In further embodiments, the elliptical trajectory is a helical trajectory or a spiral trajectory. In some embodiments, the first trajectory is a circular trajectory. In further embodiments, the circular trajectory is a helical trajectory or a spiral trajectory. In some embodiments, the second trajectory conforms to the shape of the target. In some embodiments, the second trajectory is an elliptical trajectory. In further embodiments, the elliptical trajectory is a helical trajectory or a spiral trajectory. In some embodiments, the computer-implemented method of claim 26, wherein the second trajectory is a circular trajectory. In further embodiments, the circular trajectory is a helical trajectory or a spiral trajectory.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION OF THE INVENTION

Figure 1:
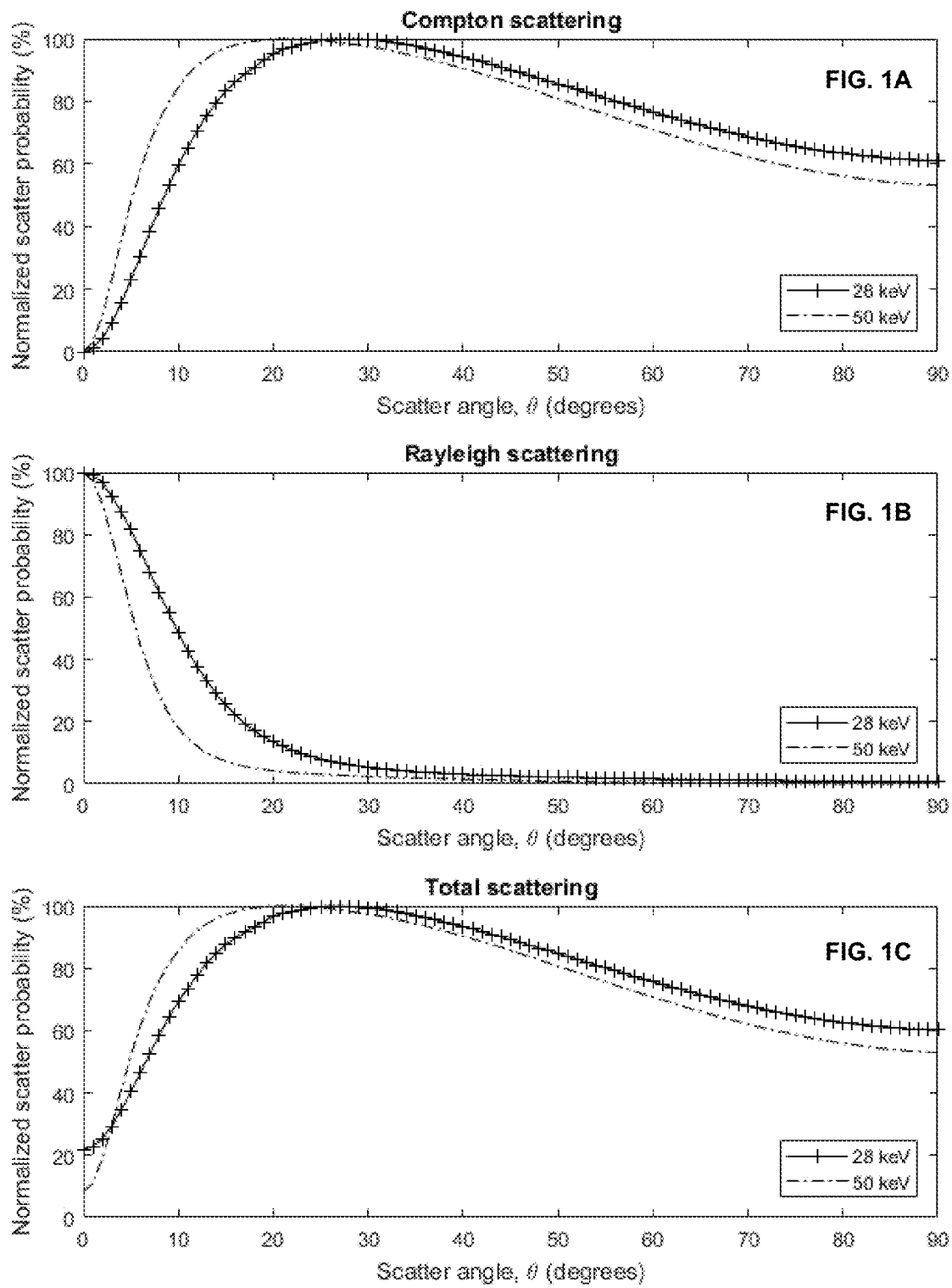
FIGS. 1A-1C are theoretically simulated distributions of different types of scattered radiation with respect to the scatter angle in soft tissue.

Described herein, in certain embodiments, are radiologic computed tomography (CT) systems comprising: a x-ray generation assembly affixed to a first rotational robotic platform, the x-ray generation assembly configured to generate a collimated beam of x-ray photons; a x-ray detection assembly affixed to a second rotational robotic platform, the x-ray detection assembly comprising at least one line detector configured to detect the beam of x-ray photons; and a controller, configured to control the first rotational robotic platform to rotate the x-ray generation assembly on a first trajectory and to control the second rotational robotic platform to rotate the x-ray detection assembly on a second trajectory, the first rotational robotic platform and the second rotational robotic platform rotating independently and in synchrony in conformity to a shape of a target to capture primary x-ray photons substantially perpendicularly incident on the at least one line detector of the x-ray detection assembly. In some embodiments, the x-ray detection assembly comprises a plurality of line detectors. In further embodiments, each line detector is independently positioned at a cone angle. In further embodiments, each line detector is independently positioned at a tilt angle. In further embodiments, each line detector is independently positioned at a distance from a focal spot of a x-ray source of the x-ray generation assembly. In some embodiments, captured scattered radiation is constrained to photons scattered less than 20 degrees from a primary path. In some embodiments, x-ray photons captured by the x-ray detection assembly are limited to x-ray photons within 20 degrees from orthogonal. In some embodiments, the target is an anatomical target. In various further embodiments, the beam has a x-ray beam energy falling within a diagnostic range of 20 keV to 140 keV. In some embodiments, the anatomical target is a human extremity. In further embodiments, the beam has a beam energy of about 50 keV. In some embodiments, the anatomical target is a human female breast. In further embodiments, the beam has a beam energy of about 25 keV. In some embodiments, the anatomical target is a whole human body. In some embodiments, the beam has a fan angle less than 2 degrees. In some embodiments, the first trajectory conforms to the shape of the target. In some embodiments, the first trajectory is an elliptical trajectory. In further embodiments, the elliptical trajectory is a helical trajectory or a spiral trajectory. In some embodiments, the first trajectory is a circular trajectory. In further embodiments, the circular trajectory is a helical trajectory or a spiral trajectory. In some embodiments, the second trajectory conforms to the shape of the target. In some embodiments, the second trajectory is an elliptical trajectory. In further embodiments, the elliptical trajectory is a helical trajectory or a spiral trajectory. In some embodiments, the second trajectory is a circular trajectory. In further embodiments, the circular trajectory is a helical trajectory or a spiral trajectory.

Also described herein, in certain embodiments, are computer-implemented methods of performing radiologic computed tomography (CT) comprising: generating, by a x-ray generation assembly affixed to a first rotational robotic platform, a collimated beam of x-ray photons; detecting, by a x-ray detection assembly affixed to a second rotational robotic platform and comprising at least one line detector, the beam of x-ray photons; and controlling, by a controller unit, the first rotational robotic platform to rotate the x-ray generation assembly on a first trajectory and to control the second rotational robotic platform to rotate the x-ray detection assembly on a second trajectory, the first rotational robotic platform and the second rotational robotic platform rotating independently and in synchrony in conformity to a shape of a target to capture primary x-ray photons substantially perpendicularly incident on the at least one line detector of the x-ray detection assembly. In some embodiments, the x-ray detection assembly comprises a plurality of line detectors. In further embodiments, the method comprises independently positioning each line detector at a cone angle. In further embodiments, the method comprises independently positioning each line detector at a tilt angle. In further embodiments, the method comprises independently positioning each line detector at a distance from a focal spot of a x-ray source of the x-ray generation assembly. In some embodiments, captured scattered radiation is constrained to photons scattered less than 20 degrees from a primary path. In some embodiments, x-ray photons captured by the x-ray detection assembly are limited to x-ray photons within 20 degrees from orthogonal. In some embodiments, the target is an anatomical target. In various further embodiments, the beam has a x-ray beam energy falling within a diagnostic range of 20 keV to 140 keV. In some embodiments, the anatomical target is a human extremity. In further embodiments, the beam has a beam energy of about 50 keV. In some embodiments, the anatomical target is a human female breast. In further embodiments, the beam has a beam energy of about 25 keV. In some embodiments, the anatomical target is a whole human body. In some embodiments, the beam has a fan angle less than 2 degrees. In some embodiments, the first trajectory conforms to the shape of the target. In some embodiments, the first trajectory is an elliptical trajectory. In further embodiments, the elliptical trajectory is a helical trajectory or a spiral trajectory. In some embodiments, the first trajectory is a circular trajectory. In further embodiments, the circular trajectory is a helical trajectory or a spiral trajectory. In some embodiments, the second trajectory conforms to the shape of the target. In some embodiments, the second trajectory is an elliptical trajectory. In further embodiments, the elliptical trajectory is a helical trajectory or a spiral trajectory. In some embodiments, the computer-implemented method of claim 26, wherein the second trajectory is a circular trajectory. In further embodiments, the circular trajectory is a helical trajectory or a spiral trajectory.

When x-rays are emitted from the x-ray tube of the CT device (or any generating source), the amount of x-ray scatter that occurs is highly dependent on the energy of the photon as well as the properties of medium that it is transitioning through. In the present case, the "medium" is the specific anatomy being imaged. The properties of a knee, which contains bone for instance, differ from those of a breast, comprised primarily of soft tissue. Two types of scatter phenomena are pervasive in the diagnostic x-ray energy range—Rayleigh (also known as coherent) scattering and Compton (also known as incoherent) scattering. FIGS. 1A-1C show the dependency of scatter probability on scatter angle. The results are derived from implementing Klein-Nishina theory for the differential cross sections of scattered photons considering the form factors observed in soft tissue. The simulated energy bins are the beam effective energies of two clinically available dedicated CT systems: a dedicated breast CT system with an effective energy of 25 keV and a dedicated extremities CT system with an effective beam energy of 50 keV. The total scattering probability (FIG. 1C) is calculated based on the weighted summation of Compton (FIG. 1A) and Rayleigh (FIG. 1B) scattering given the probability of each scattering type happening in soft tissue. As shown, scattered photons are least likely to be diffracted from the original path when scatter angle is close to zero. This implies that if x-ray detector designed for the CT system covers a narrow beam (e.g. with a fan angle less than 2 degrees), it only covers a small portion of the diffracted photons and hence, the more probable scattered photons are not captured. This provides a hypothesis for employing a narrow-beam image acquisition paradigm instead of the traditional means of image acquisition used in dedicated CT systems.

In addition to the negative impacts of scattered radiation, artifacts arise in reconstructed CT images due to the difference of path lengths between that of the shortest and longest rays traversing through the space between the focal spot and sensitive detector elements. The larger the deviation of the incident ray angle from perpendicular, the more severe the artifacts. Generally, it is always desirable to keep the incident angle close to perpendicular.

Figure 2:
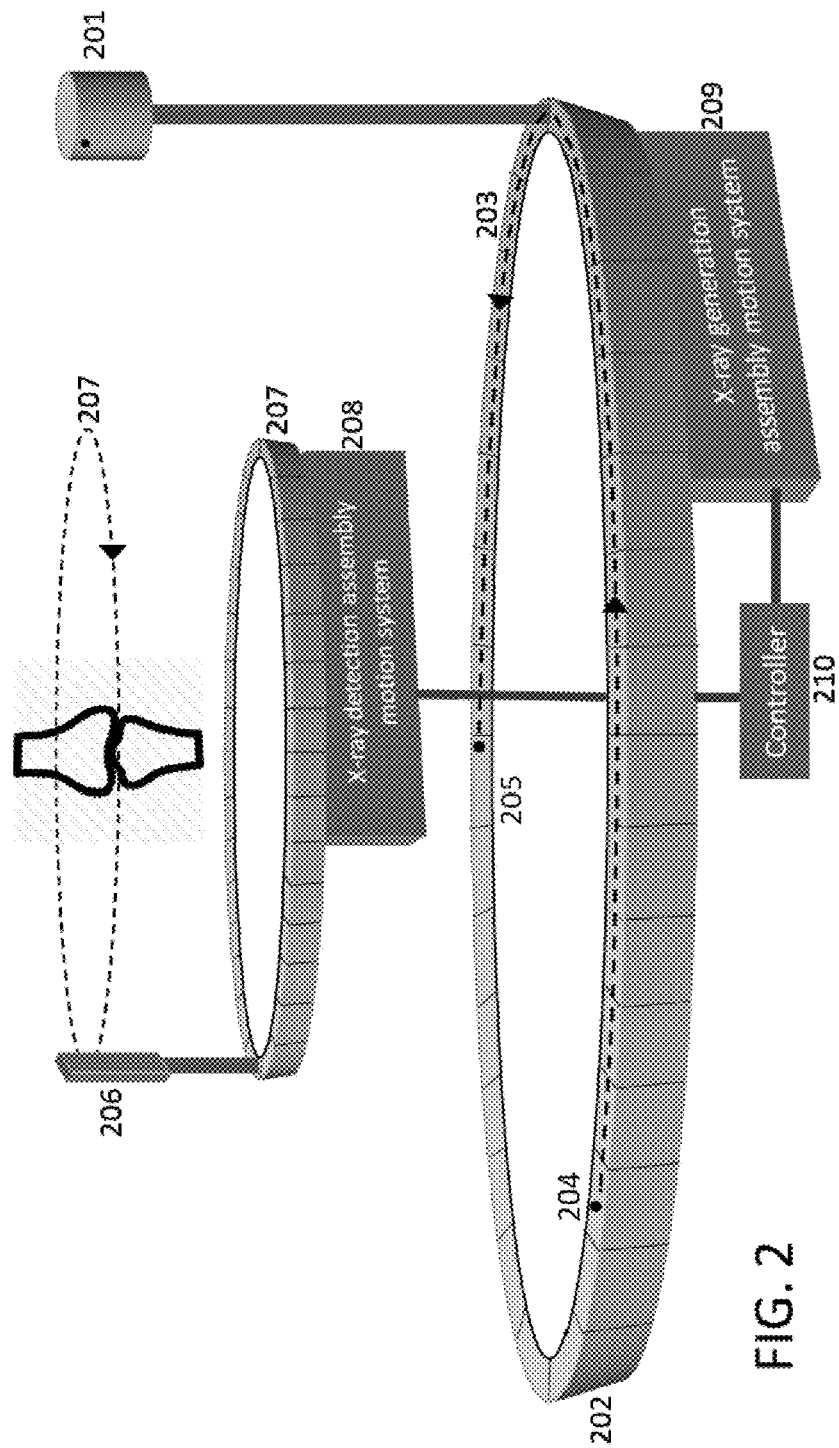
FIG. 2 is a prospective view that shows the configuration of the imaging apparatus for lower extremity imaging.

FIG. 2 shows an embodiment of the invention, an apparatus for scanning an extremity of human body, in this case a knee. The hardware that is depicted in FIG. 2 are the main components of the imaging system assembly which includes an x-ray generation assembly, the x-ray detection assembly and the robotics associated with the image acquisition around the knee. X-ray generation assembly 201 is physically attached to the x-ray generation robotics assembly 202. Rotation of the x-ray generation robotics assembly 202 results in translating the x-ray generation assembly 201 through an elliptical trajectory 203 from a start position 204 to a stop position 205. Robotically independent from the x-ray generation assembly is the x-ray detection assembly which consists of a narrow beam detector 206 that is attached to the x-ray detection robotics assembly 207. The motion of the x-ray detection robotics assembly results in rotation of the x-ray detector 206 around the knee through a circular trajectory 208. The motion of the x-ray detection assembly is controlled by a motion control unit 209. The motion of the x-ray generation assembly is controlled by a separate motion control unit 210. The synchronization of the movements is made possible through a central control unit 211.

Figure 3:
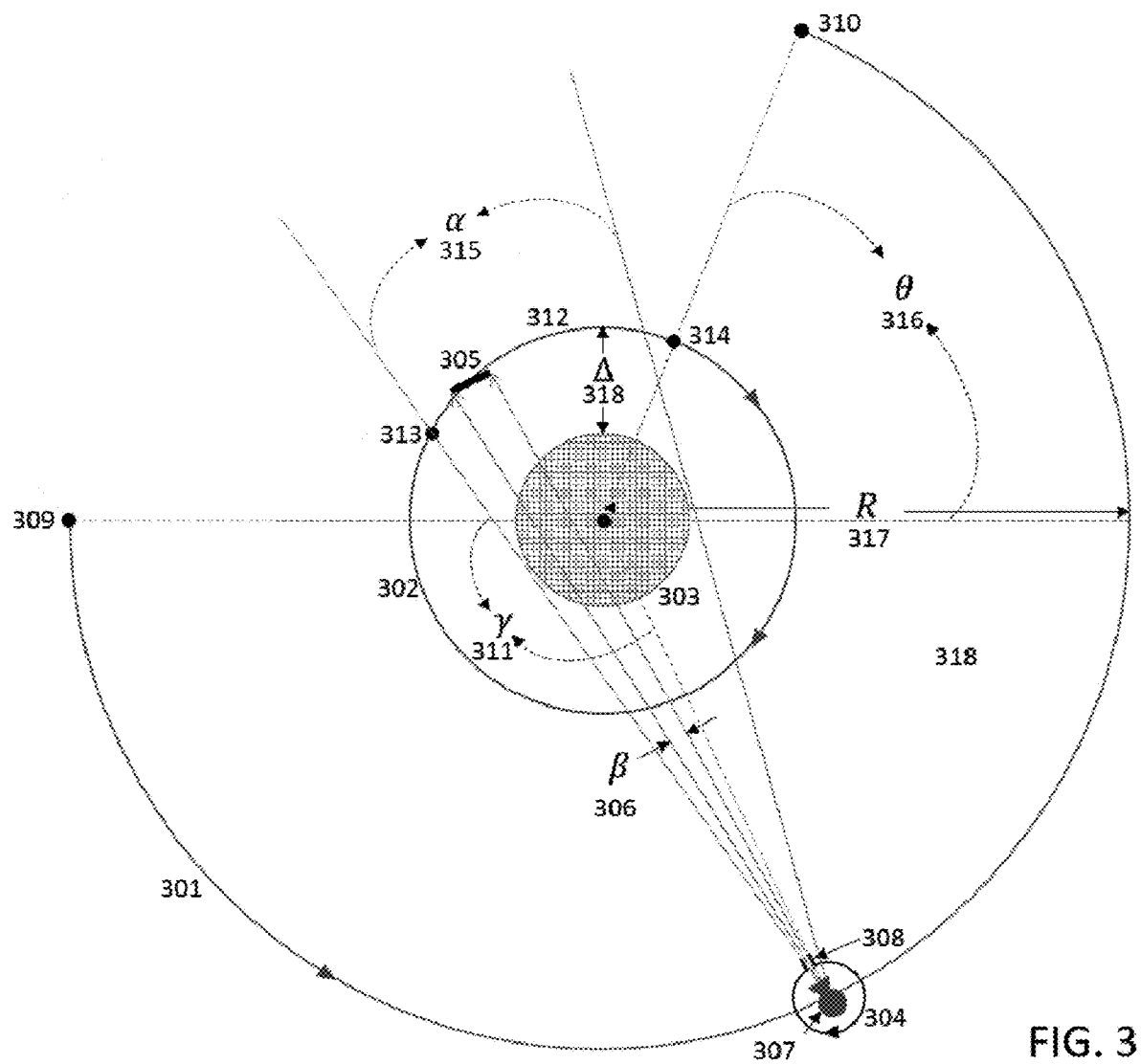
FIG. 3 is a schematic view showing the geometry of the imaging apparatus with collimator ring attached to the x-ray generation assembly.

FIG. 3 illustrates an embodiment of the imaging system and positioning and movement of its components with respect to a patient's anatomy as seen from the top. The trajectory of the x-ray production assembly is elliptical. The circular path 301 shown in FIG. 3 is a special case of the elliptical trajectory. The trajectory of the x-ray detection assembly's movement is circular 302. The anatomical feature is positioned within the FOV 303 of the imaging system. During an image acquisition, an x-ray beam is produced and collimated in the x-ray production assembly 304. The x-ray beam's photons interact with the anatomical feature located within the FOV. After passing through the anatomy, the beams are captured by a detector panel 305, following which they are converted into a raw digital image. Assuming a 100% detection quantum efficiency (an ideal x-ray detector), the positioning and moving trajectories of the imaging system are designed so that all primary transmitted x-rays within a collimated beam β 306 are captured by the detector panel 305. The x-ray production assembly 304 consists of an x-ray tube 307, a rotating collimator disk with an opening (a small window) 308 for collimating the fan angle of the beam exiting the x-ray tube system, and the robotics necessary for controlling the movement of the tube and collimators. The depicted opening 308 controls the fan angle of the x-ray beam. The assembly follows a circular arc trajectory 301 from a start position 309 to a stop position 310.

Depicted in FIG. 3 is a position of the x-ray production assembly where the focal spot's angular displacement from the starting position of the scan is denoted by γ 311. During this movement, the x-ray production assembly generates n cumulative projections. A cumulative projection is defined as patching all the projections acquired by detector panel 305 while it spans an arc 312 which is a part of the detection assembly trajectory path 302. During each cumulative projection, the detector panel sweeps in a trajectory following this arc from a start position 313 to an end position 314. During this motion, p projections are captured by the detector panel 305 along the cumulative fan angle α 315. The cumulative fan angle is the union of the smaller fan angles β 306 during a cumulative projection acquisition where the detector panel 305 moves along an arc 312 from a start position 313 to an end position 314, while capturing raw images. For all cumulative projections, the relationship between the cumulative fan angle (α), the number of narrow angle projections (p) and each individual projection's fan angle (β) is α=p×β. The angular span of the x-ray production assembly rotary movement falls within 0 and π+θ, where θ 316 must follow the inequality α<θ<π. This requirement is necessary for a successful CT image reconstruction. The radius of the x-ray production movement, R 317, and the gap between the x-ray detection arc 312 and FOV 303, denoted by Δ 318, are the parameters that define the CT system's magnification factor for each reconstructed voxel within the FOV.

Figure 4:
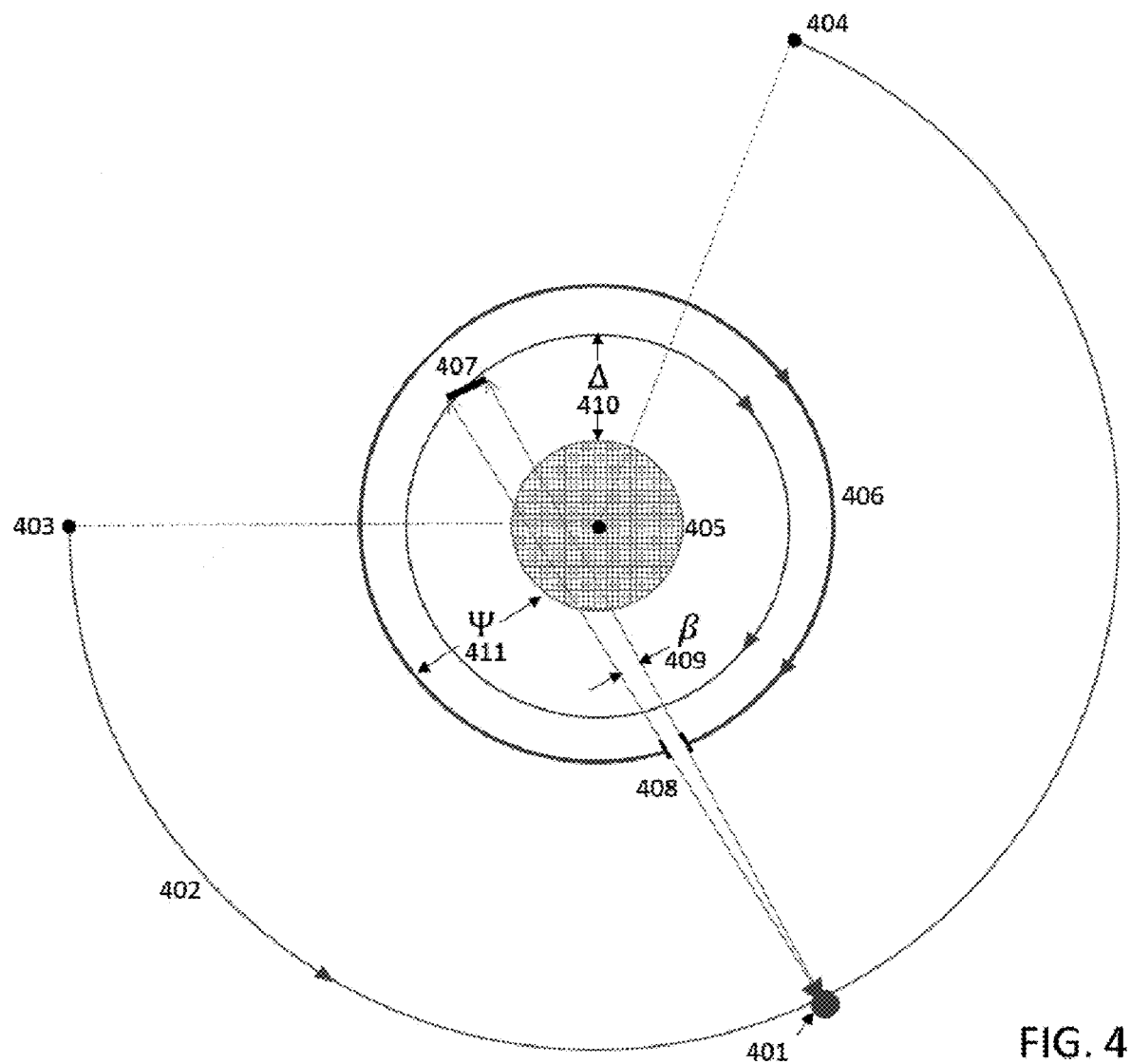
FIG. 4 is a schematic view showing the geometry of the imaging apparatus with collimator ring attached to the x-ray detection assembly.

FIG. 4 shows a special case of the embodiment shown in FIG. 3. Here the collimator is positioned on the x-ray detection assembly rather than the x-ray generation assembly. The scan protocol is the same: The x-ray tube 401 translates along an elliptical path 402 (circular trajectory is a special case of elliptical trajectory) from a start position 403 to an end position 404 while projecting x-rays on the object positioned in the FOV 405 of scanner. The detection assembly enclosure contains a circular collimator 406 that rotates in synchrony with the detector panel 407 so that a collimated x-ray beam is permitted through an opening 408 to enter the FOV with a fan angle of β 409. The transmitting photons within this beam are captured by the detector panel and turned into raw projection images. The rotational centers of the detector movement trajectory and collimator circular ring overlap with the detector panel positioned with a distance Δ 410 and collimator ring positioned with a distance Ψ 411.

The design outlined in FIG. 3 provides image acquisition trajectories that can be modulated depending on the shape and size of the anatomy. The primary goals remain the same: to keep the scattered radiation accumulation at a minimum level and to keep the incident angle of the x-rays as close to perpendicular as possible.

Figure 5C:
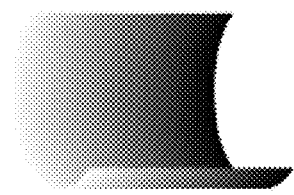
FIGS. 5A-5U are a series of schematic and prospective views showing the projection conformations resulting from different anatomies, motions of the imaging systems and their relative set up.
Figure 5B:
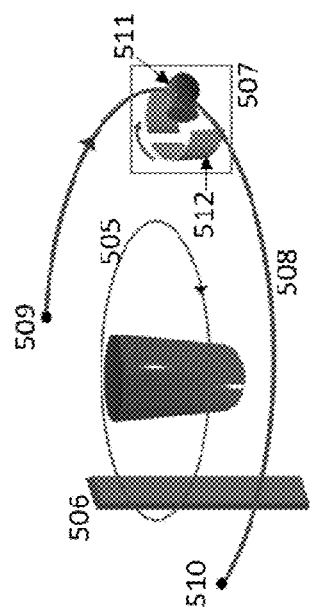
Figure 5A:
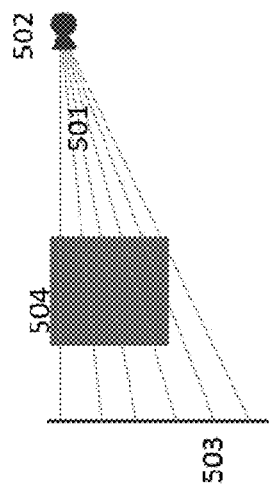
Figure 5F:
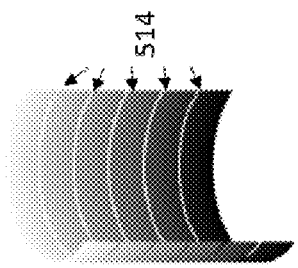
Figure 5E:
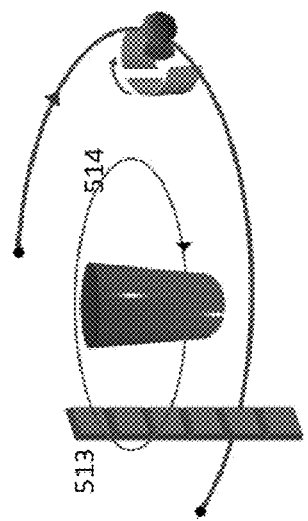
Figure 5D:
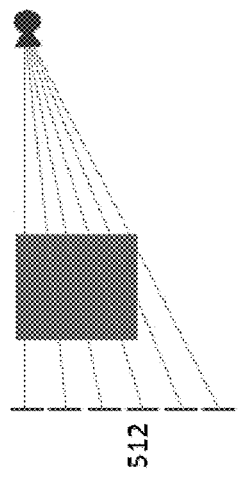
Figure 5I:
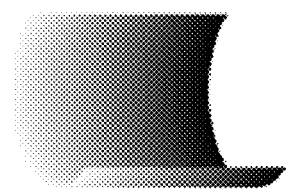
Figure 5H:
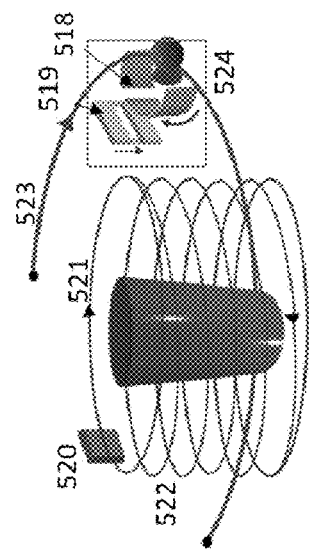
Figure 5G:
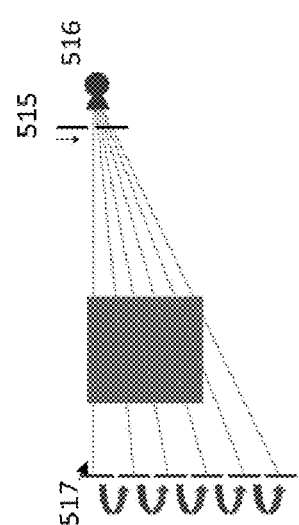
Figure 5L:
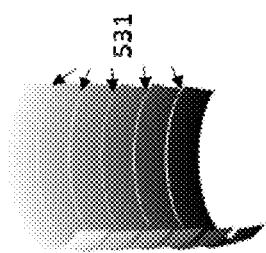
Figure 5K:
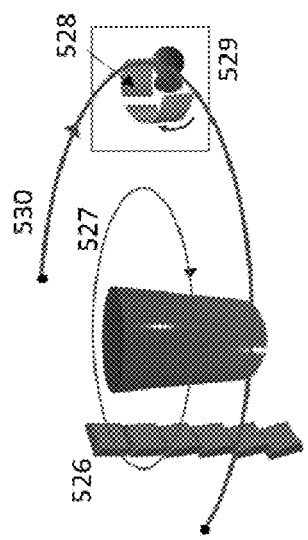
Figure 5J:
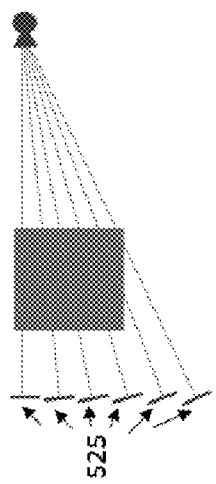
Figure 5O:
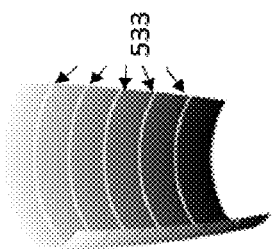
Figure 5N:
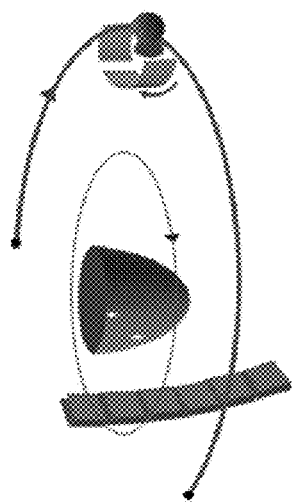
Figure 5M:
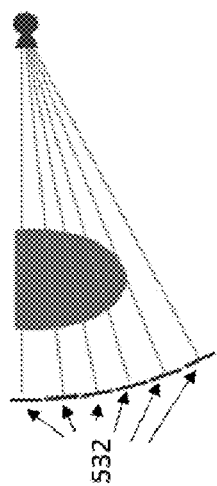
Figure 5R:
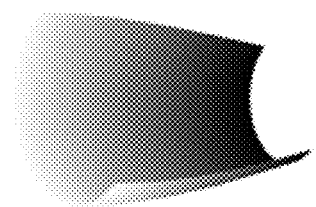
Figure 5Q:
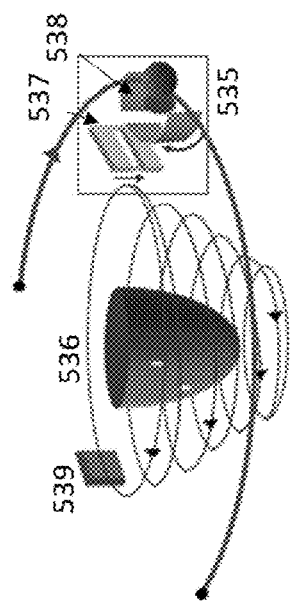
Figure 5P:
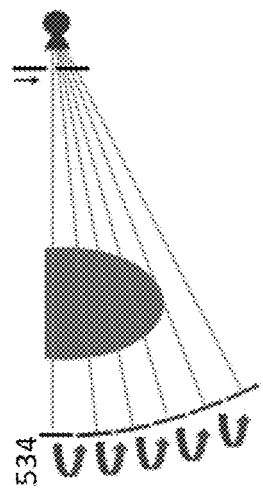
Figure 5U:
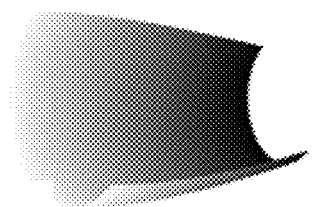

FIGS. 5A-5U show examples of the x-ray detector panel, beam shape, detector and tube trajectories and the resulting x-ray detection loci associated with each combination. Each row represents a combination. The left column shows the layout of the x-ray tube, beam and detector with respect to an anatomical feature. The middle column presents an oblique view of the system geometry along with the x-ray generation and detection assemblies' moving paths. The right column is the swept loci of the detector panel along its trajectory during a projection acquisition. In FIG. 5A, the x-ray collimator system is set up such that the generated photons 501 at the x-ray production assembly 502 form a narrow vertical shape that is captured by detector panel 503. The vertical size of the detector panel 503, regardless of its manufactured specification, is a parameter that depends on the geometry of the x-ray system and the length of the anatomy 504. The oblique view shown in FIG. 5B highlights the circular trajectory 505 of the x-ray detector panel 506 around the anatomy. In this case, as well as the cases illustrated in FIGS. 5D-5L, the contour of the anatomical feature resembles a cylinder. Anatomical examples of for which this set up applies are extremities such as arms or legs. During a scan, x-ray generation assembly 507 follows an elliptical path 508 from a start point 509 to a finish point 510. This elliptical path can be reduced to a circular path with its center coincident with the center of the circular path of detector panel. The angular span of this path lies between zero and at least $\pi+\alpha$, where $\alpha$ is the accumulated projection fan angle previously described in FIG. 3. The components of the x-ray production assembly in this case are the x-ray tube 511 and a rotating x-ray collimating disk 512 and associated robotics. The movement of the collimating disk is synchronized with that of the detector panel 506 such that both have the same phase and frequency. During a scan, several projections are made, each captured when movement of the detector panel 506 creates a cylindrical locus shown in FIG. 5C.

Difficulties in manufacturing or utilization of a detector panel with a large cone beam coverage such as 503 may lead to combining small detector panels via horizontal abutting to generate an assembly of detector panels 512 as shown in FIGS. 5D and 5E. This detection setup provides the same axial coverage as described before in FIGS. 5A and 5B. In this geometry, the positioning and movement of the x-ray generation assembly and detector panels 513 are similar to those shown in FIGS. 5A and 5B. During a single projection and image acquisition, movement of the detector panel 513 along a circular path 514 as depicted in FIG. 5E results in forming a semi cylindrical locus displayed in FIG. 5F. The gaps 514 between individual detector pieces used in detector panel 513 need to be algorithmically corrected to avoid introducing severe artifacts in the reconstructed images.

The large cone angle span of the described detector panels 503 and 512 results in capturing some scattered radiation that leads to a decreased contrast resolution in the reconstructed images. A solution is to utilize the robotics of the x-ray production and detection assemblies to generate a circular-spiral path for a detector panel with small fan and cone angles coverage. This geometry is illustrated in FIG. 5G and FIG. 5H. A vertically translating collimator 515 is added to the x-ray generation assembly to collimate the cone beam angular span of the x-rays generated at x-ray tube 516. The size of the detector panel 517 and geometry of the system is set such that it fully covers the output x-ray beam's cone angle. Therefore, the x-ray collimation is composed of two collimating units, a rotating fan angle collimating disk 518 and a vertically translating cone angle collimating surface 519 both moving in synchrony with the detector panel 520 such that the detector panel's surface is along the path of the primary x-ray photons generated by the x-ray production assembly and transitioned through the anatomy positioned in FOV. Moving along the vertical direction, the detector panel follows a circular path 521 followed by a spiral path 522. The combined trajectory results in the entirety of anatomy being along the x-ray path in each x-ray projection and acquisition sequence. The movement path 523 of the x-ray generation assembly 524 is similar to the ones described in FIGS. 5B and 5E. A combined projection image is assembled when the detector panel's movement during x-ray projection and image acquisition follows a semi cylindrical locus such as one shown in FIG. 5I.

As the cone angle increase, the cylindrical x-ray detection loci outlined in FIGS. 5C, 5F and 5I implies capturing primary photons that are not perpendicular to the surface of the detector panel. A large deviation from the perpendicular incidence of x-ray photons during image acquisition results in induced cone-beam artifacts in the reconstructed images and consequently, reducing the image quality. This issue is addressed in the following four scan geometry designs shown in FIGS. 5J-5U.

FIG. 5J illustrates a setup where the x-ray detector is assembled through laying out individual detector panels 525 such that the angle between the incident primary photons on each panel and the panel's surface is close to perpendicular. The assembled detector panel 526 follows a circular trajectory 527 in each x-ray projection and acquisition sequence like that described in FIGS. 5B and 5F. A fan angle collimating disk 528 is used in synchrony with the assembled detector panel such that the detector panel is on the path of all generated primary photons exiting the x-ray production assembly 529. The x-ray production assembly follows a trajectory 530 similar to that discussed in FIGS. 5B, 5E and 5H. The traced x-ray detection locus during each projection acquisition is shown in FIG. 5L. The gaps 531 between the individual panels need to be corrected in the acquired projection images prior to image reconstruction to avoid severe artifacts caused by partial sampling and focal spot penumbra effect.

FIG. 5M illustrates a setup where the individual detection panels 532 are placed such that cone beam artifacts are reduced, by positioning each piece in an inclined angle with respect to adjacent panels. They are also shifted horizontally to minimize the gap between the individual detecting pieces. This geometry is ideal for anatomical features with a variable diameter, such as the breast or the human head. The geometry of the system, positioning of the components with respect to anatomy, and movement of the rotating and translating parts of the CT system are similar to that outlined in FIG. 5N. The swept detection locus during a projection image acquisition is shown in FIG. 5O. Although the gaps between the individual detecting pieces observed in FIG. 5L is reduced, the remaining gap reflected in the traced detection trajectory 533 is required to be corrected before image reconstruction. In addition, the large cone beam coverage means increased scattered radiation pileup in the acquired projections which reduces the contrast resolution of the reconstructed images.

FIGS. 5P, 5Q and 5R show a setup where a single detector panel 534 is used to detect the primary photons generated at the x-ray generation assembly 535. The size of the detector panel does not encompass the dimensions of the entire breast as in existing dedicated breast CT technologies. Rather, in the present design, the x-ray detection assembly causes the detector panel to follow a circular-spiral trajectory 536 in synchrony with cone beam 537 and fan beam 538 collimating units such that the entire anatomy is imaged and all the primary x-ray photons that exit the x-ray production unit 535 are captured by the detector panel 539. X-ray generation assembly follows the same path as the one previously described in FIGS. 5B, 5E, 5H, 5K and 5N. The traced locus created by the movement of the detector panel during a projection image acquisition is displayed in FIG. 5R. The generated projection most resembles the shape of a breast where a minimal level of scattered radiation is captured and the photons incident on the surface of detector panel perpendicularly.

Figure 5T:
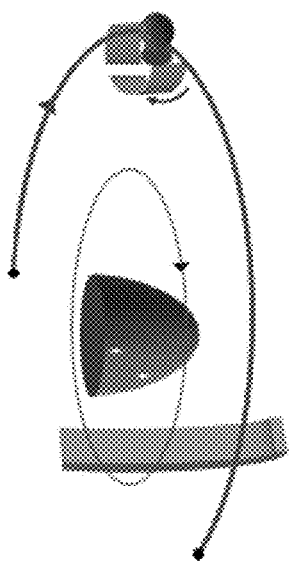
Figure 5S:
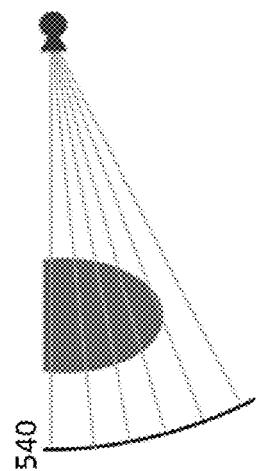

FIGS. 5S, 5T and 5U illustrate additional instances of detector panel formations and movements. The detector panel 540 embodies a continuously curvature along vertical direction. This geometry enables a close to perpendicular ray incidence on the surface of the detector panel. The traced path of the detector panel's movement during an image acquisition is displayed in FIG. 5U.

There are technical limitations associated with some of the setups illustrated in FIGS. 5A-5U. For instance, the correction for the gaps observed in projection images in setup combinations displayed in FIGS. 5F, 5L and 5O comprises of a form of interpolation to engage the neighboring detector elements in synthesizing values for the unsampled locations within gaps. Hence, a synthesized detector element value is not a true representative of the line integral between the detector element and the focal spot. The spiral trajectory demonstrated in FIGS. 5P and 5Q requires rapid mechanical movements of the detector panel and collimator assembly that is challenging to implement. Finally, the detector panel shape suggested in FIG. 5S is rigid and is not flexible to fit different anatomies.

Figure 6A:
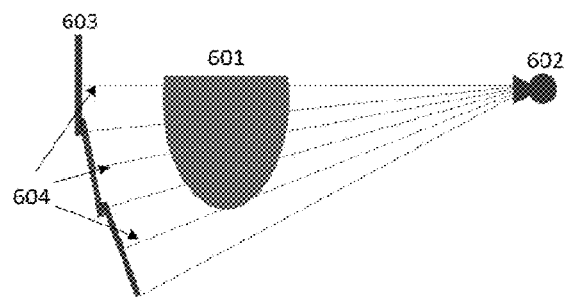
FIGS. 6A-6D are schematic and prospective views showing the projection conformations resulting from imaging a pendant breast, motions of the imaging systems and their relative set up.
Figure 6B:
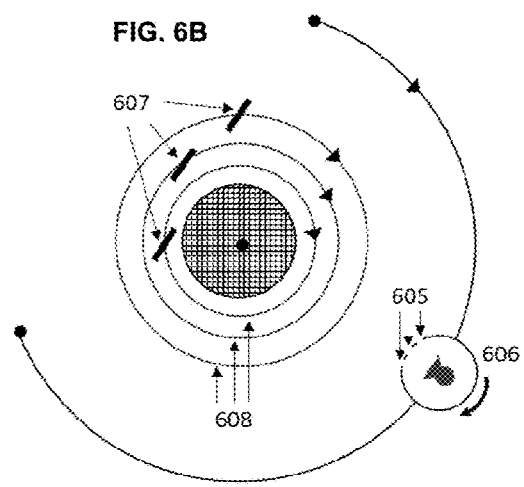
Figure 6C:
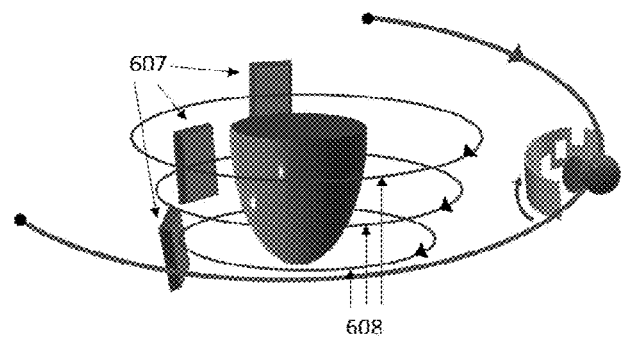
Figure 6D:
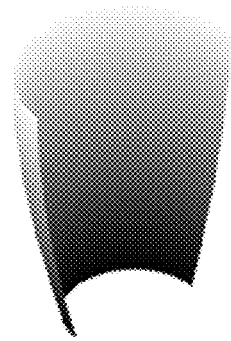

FIGS. 6A-6D illustrate an embodiment of the invention where multiple detectors positioned at different cone angles, and with appropriate distance from each other (to reduce the scattered radiation received at each panel) are transitioned along the concentric circles around a breast. Only three detector panels are shown in FIGS. 6A-6D. More panels may be used. FIGS. 6A-6D show the setup of the imaging components with respect to the anatomy from a side view (FIG. 6A), top view (FIG. 6B) and oblique view (FIG. 6C). FIG. 6D is the swept loci of the detector panel assembly 603 after completing its trajectory during a projection acquisition, demonstrating the achieved conformation to the anatomical shape of the anatomy 601 within the FOV. The object 601 is positioned between the focal spot 602 and the detector panel assembly 603. The detectors within the assembly are placed at an angle relative to each other to ensure a perpendicular angle between the detector panels and the primary rays 604. The positioning of the detector panels and the trajectory of each single panel's movement are indicated such that there is no gap between the traced trajectories of the panels. The collimator ring 605 contains openings (or windows) that align with the detector panels such that the primary x-ray photons exiting the x-ray generation assembly 606 are captured by the detector panels 607. The detector panels rotate around the object along concentric circles 608. The orientation of the detector panels is controlled such that their surfaces are perpendicular to a line which connects the focal spot and the axis of rotation of the detectors. The radius of each panel's trajectory is set based on the size and shape of the object in FOV.

Utilizing line detectors in the design of the x-ray detection assembly enables bilateral imaging of parts of the body that is not achievable via traditional dedicated CT systems such as cone beam or helical. An example is bilateral imaging of both breasts of a female patient during a single acquisition sequence without the need for repositioning. Based on the geometry outlined in FIG. 3, the breasts of a patient are scanned one at a time. First, patient is positioned on the scanner table top so that a breast is placed into the FOV of the imaging system and a scan procedure is performed. This is followed by repositioning of the patient such that the patient's other breast is placed inside of the FOV and a second scan procedure is performed. If the scan protocol includes contrast enhancement, a contrast enhancement agent is administered between the pre-contrast and post-contrast scans which implies another repositioning of the patient is necessary such that both breasts are imaged pre- and post-contrast agent administration. The multiple repositioning of the patient can result in an extended scan time and patient discomfort. In addition, pre-contrast and post-contrast images acquired before and after patient repositioning may look substantially different since the body parts that are of any interest in breast cancer imaging are mainly soft tissue and undergo deformations during repositioning attempts. Therefore, some anatomy of the same breast may be visible in one image, either pre-contrast or post-contrast, and in not the other. In addition, attempts to correct for non-rigid soft-tissue deformations require complex and often suboptimal image registration methodologies. Another example is the musculoskeletal extremity imaging under a weight-bearing condition where a scan procedure entails acquiring projections from both legs of a standing person. The solution to the stated set of problems is imaging both anatomies without repositioning.

Figure 7:
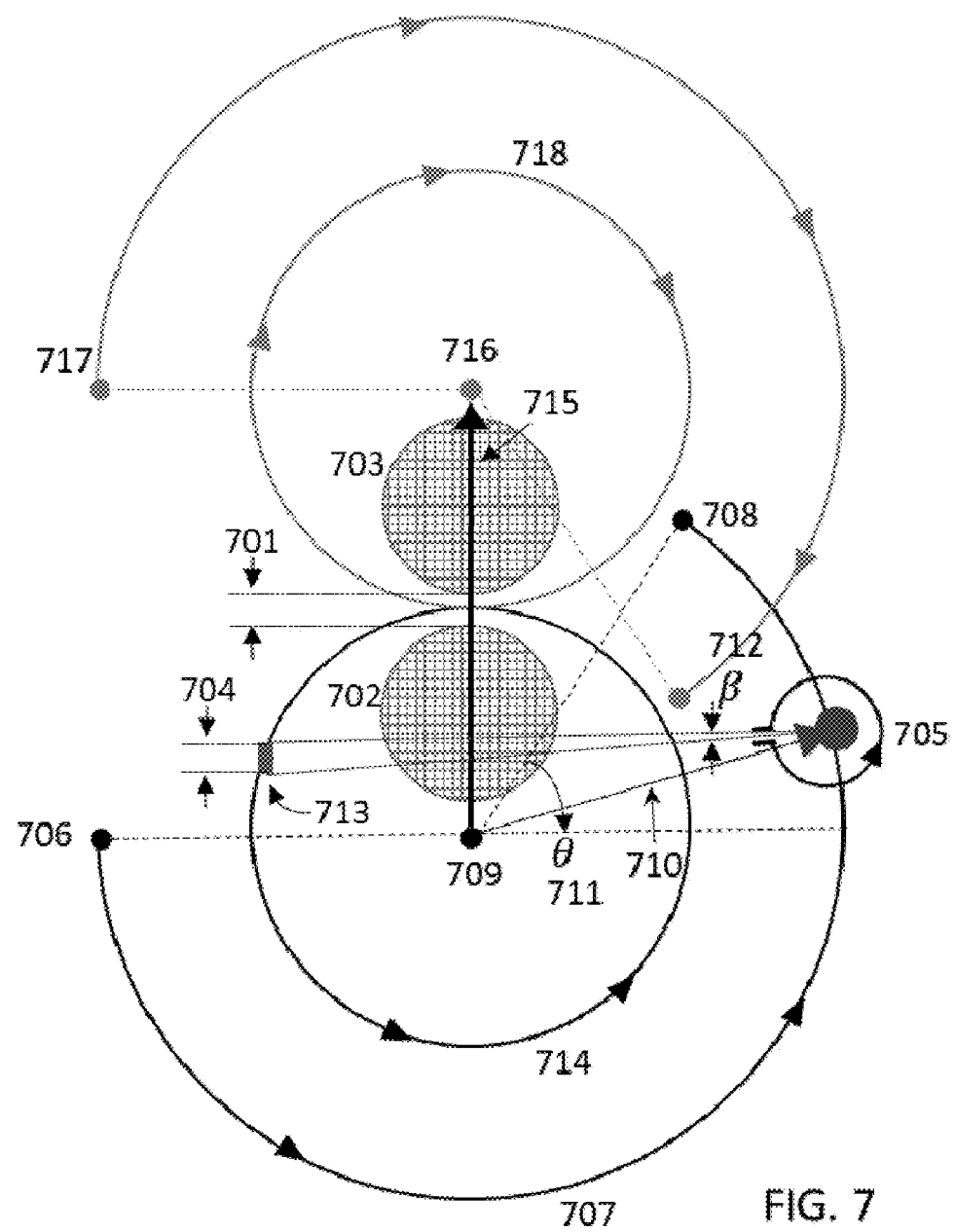
FIG. 7 is a schematic view showing the geometry of an embodiment of the bilateral imaging apparatus.

FIG. 7 shows an embodiment of the scanner system's geometry as observed from above where both organs (breasts or legs) of a patient are scanned without a need for repositioning. One x-ray production assembly and an x-ray detection assembly are used for the geometry used in FIG. 7. The x-ray production assembly is like that shown in FIG. 3, where the fan angle coverage of the generated x-ray beam is collimated so that the detector panel is on the path of the primary x-ray photons. The organs of interest are positioned within the FOVs and scanned sequentially. The shortest distance 701 between the perimeters of the first FOV 702 and second FOV 703 is determined based upon several primary considerations. First, it minimizes the patient's discomfort arising from manipulation or spreading of the organs apart from one another. Second, the maximum volumes of the anatomies of interest are imaged. Third, the gap 701 is greater that the detector panel's width 704. Using this geometry, a routine scan protocol involves positioning a patient such that both organs (e.g. breasts or legs) are placed within the FOVs, followed by a two sequential CT scans. The x-ray generation assembly 705 is placed at a start position 706 and moved along an elliptical path 707 to reach a stop position 708.

The circular trajectory shown in FIG. 7 is a special case where focuses of the elliptical trajectory coincide at a single point 709. At every point of the elliptical path, the x-ray tube faces the center of rotation of the x-ray detection assembly 709 such that an imaginary line 710 drawn from this point to the tube's focal spot is normal on the surface of the tube's anode. The angular coverage of the circular path, $\theta$ 711 must be between $\pi$ and $\pi+\alpha$, where $\alpha$ is the fan angle of the x-ray generation assembly when imaging the FOV 702. Similar to the case described in FIG. 3, the fan angle coverage of x-ray production assembly, $\beta$ 712, is set such that the detector panel 713 is along the path of the primary photons. During a single breast scan, several accumulated projections are acquired. For each accumulated projection, the x-ray detection assembly rotates along a circular path 714 such that all voxels within an FOV are covered. After a single breast scan is complete, the x-ray production and detection assemblies are translated along a path 715 from original position 709 to a new position 716 to enable scanning the other organ. During this translation, both x-ray tube and detector panel remain stationary to avoid a collision with the objects in FOV. Upon completion of translation and prior to initiation of the second scan, the x-ray generation assembly is brought back a start position 717, x-ray detection assembly is brought to a nominal rotating velocity along its circular path 718 and the fan angle collimator is synchronized in phase and rotation velocity with the detector panel.

Figure 8:
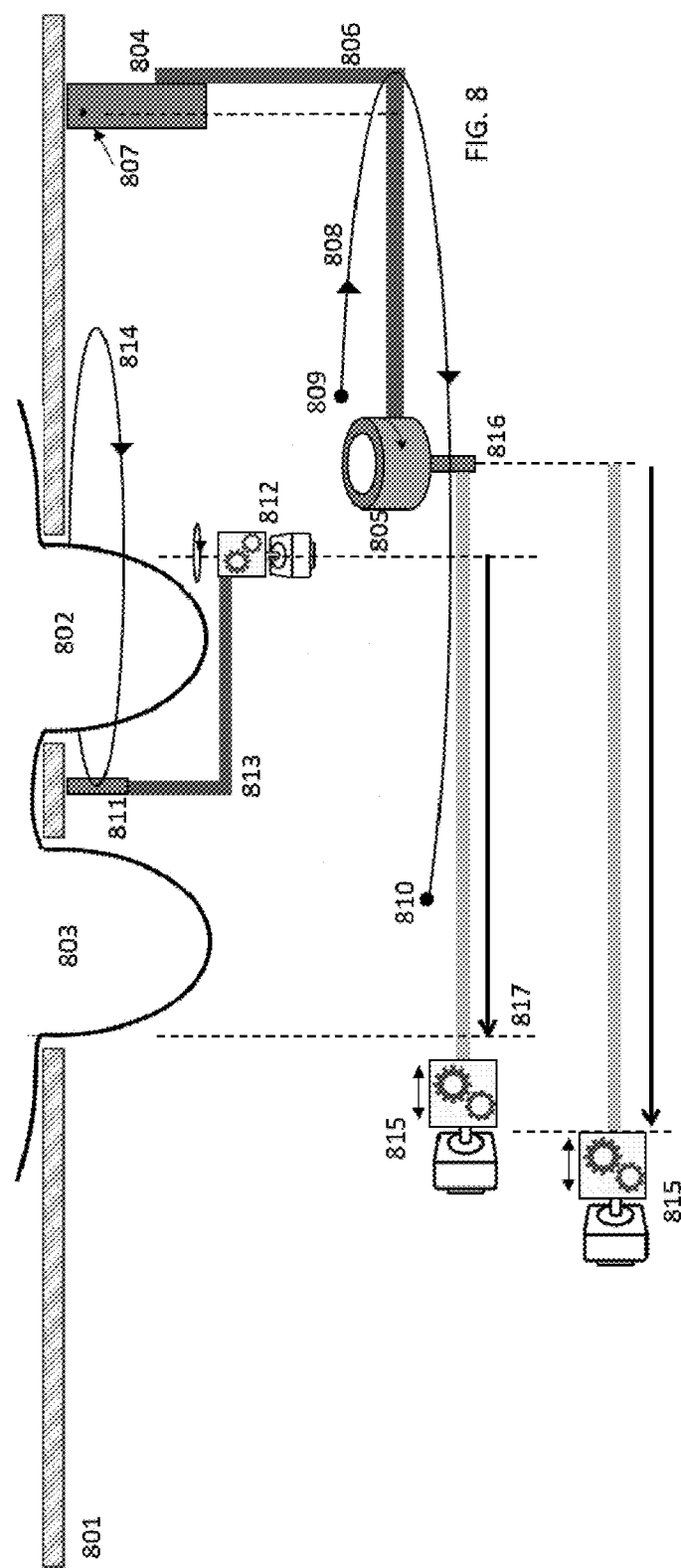
FIG. 8 is a prospective view showing the geometry of the bilateral breast apparatus.

FIG. 8 provides an example for the embodiment outlined in FIG. 7. In this case, the anatomies of interest are the left and right breasts of a patient. The patient is laid on the scanner table top 801 such that the breasts 802 and 803 are pendent in the space underneath. The imaging system components are positioned to scan the first breast. The x-ray generation assembly 804 is connected to an actuator system 805 through a hardware link 806 that causes the x-ray tube's focal spot 807 to follow an elliptical trajectory 808 from a starting point 809 to a stopping point 810. During this motion, an x-ray beam is collimated and emitted onto the breast. The x-ray detection assembly is on the path of the primary photons that are generated and transmitted through the breast. The detector panel 811 is connected to a rotary actuator system 812 through a hardware link 813. The rotary motion of the actuator forces the detector panel to follow a circular trajectory 814 around an axis of rotation 815. Upon completion of a breast scan, an actuator system 815 translates the imaging assemblies and their connected robotics from the first axis of rotation 816 to the second axis of rotation 817 through a linear path 818. This motion is followed by a similar procedure that results in scanning the patient's second breast 803.

The translation shift of the x-ray production and detection assemblies may result in changing the relative positioning of these assemblies with respect to each other which requires a new geometric calibration prior to image reconstruction. One solution to this is the use of two x-ray production assemblies and two x-ray detection assemblies. The advantages of this change are a reduction in the overall patient scan time and a reduction in patient discomfort. The reduction in discomfort in the case of breast imaging is due to the need for a single breath hold for scanning both breasts, as opposed to two sequential breath holds necessary for the geometry shown in FIG. 8.

Figure 9:
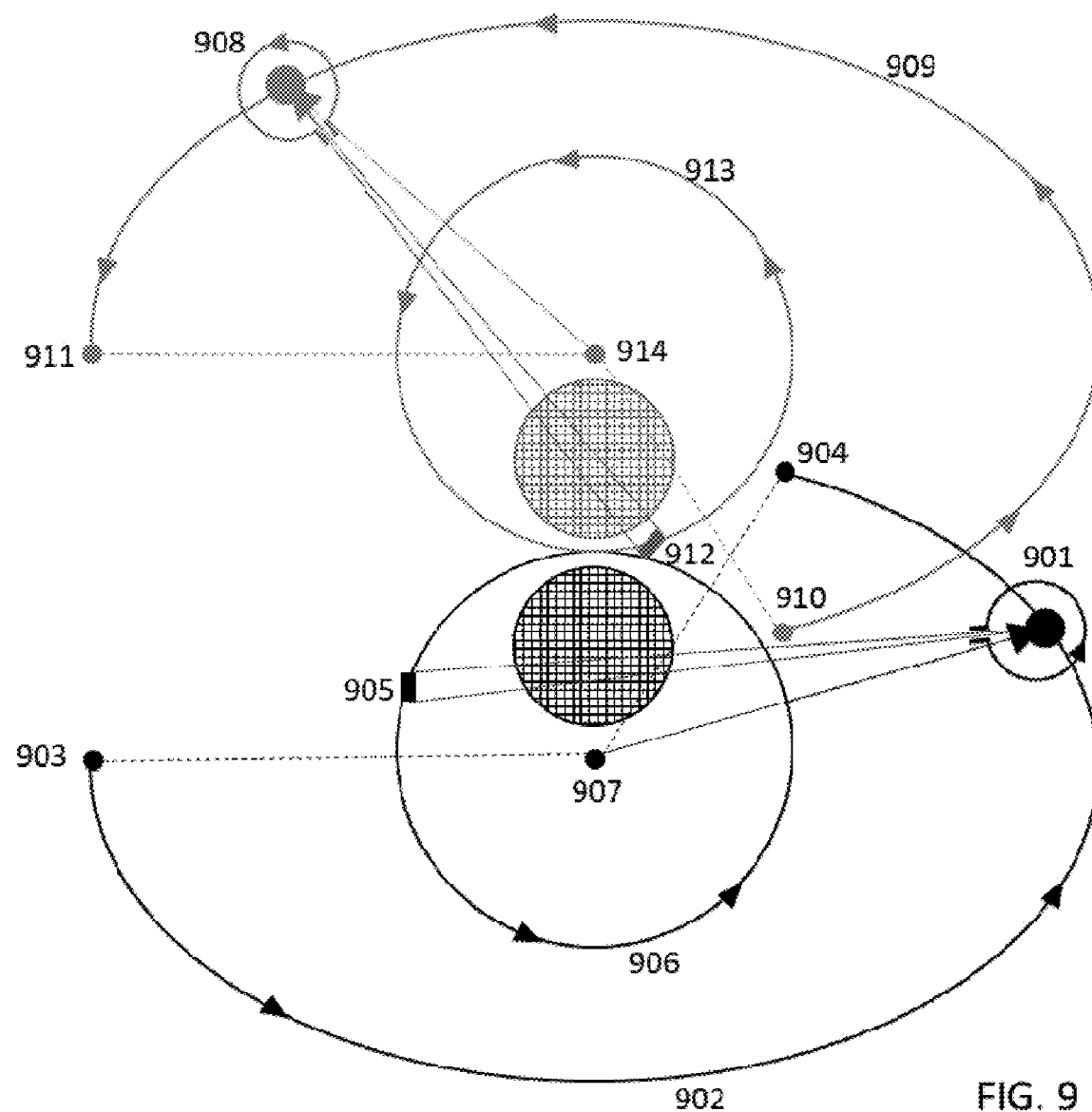
FIG. 9 is a schematic view showing the geometry of yet another embodiment of the bilateral imaging apparatus.

FIG. 9 illustrates a case where two x-ray production/detection assembly pairs are used, each pair for scanning one anatomical feature. The scan procedure for each breast is the same as what was described in FIG. 3. One x-ray production assembly 901 follows a trajectory 902 from a start position 903 to stop position 904 while the x-ray detector panel 905 rotates along a circular path 906 around a center point 907. A similar setup is designed for imaging the other breast as an x-ray production assembly 908 follows an elliptical trajectory 909 (circular trajectory is a special case of the elliptical trajectory) from a start position 910 to a stop position 911 while projecting x-ray on a detector panel 912 that is spinning along a circular path 913 around a center point 914. The spinning speed and phase of the detector panels must be set such that panels do not collide.

In general, implementations of the disclosed embodiments thus far may result in an x-ray detection assembly rotation speed of a few hundred revolutions per second. This is dependent upon the diameter of the circular trajectory, the diameter of the anatomical feature, the size of the detector panel, the intended number of accumulated projections, and the trajectory and span of the focal spot. In the case that low x-ray photon quanta are received at the detector, the TDI mode may be used during the image acquisition in the detector panel.

In TDI mode, the rotation of the x-ray detection assembly is synchronized with the readout of the detector panel, enabling continuous accumulation of signal. In this mode, the rotation speed of the x-ray tube focal spot is a small fraction of the rotation speed of the detector panel. Therefore, the position of the x-ray generation assembly is assumed to be fixed for TDI mode synchronization setup. The detector rotation speed is set such that the detector movement during acquisition of all columnar lines of the detector panel is equal to the number of columns times the width of each line. This improves sensitivity of the detector panel while reducing the noise buildup.

Figure 10:
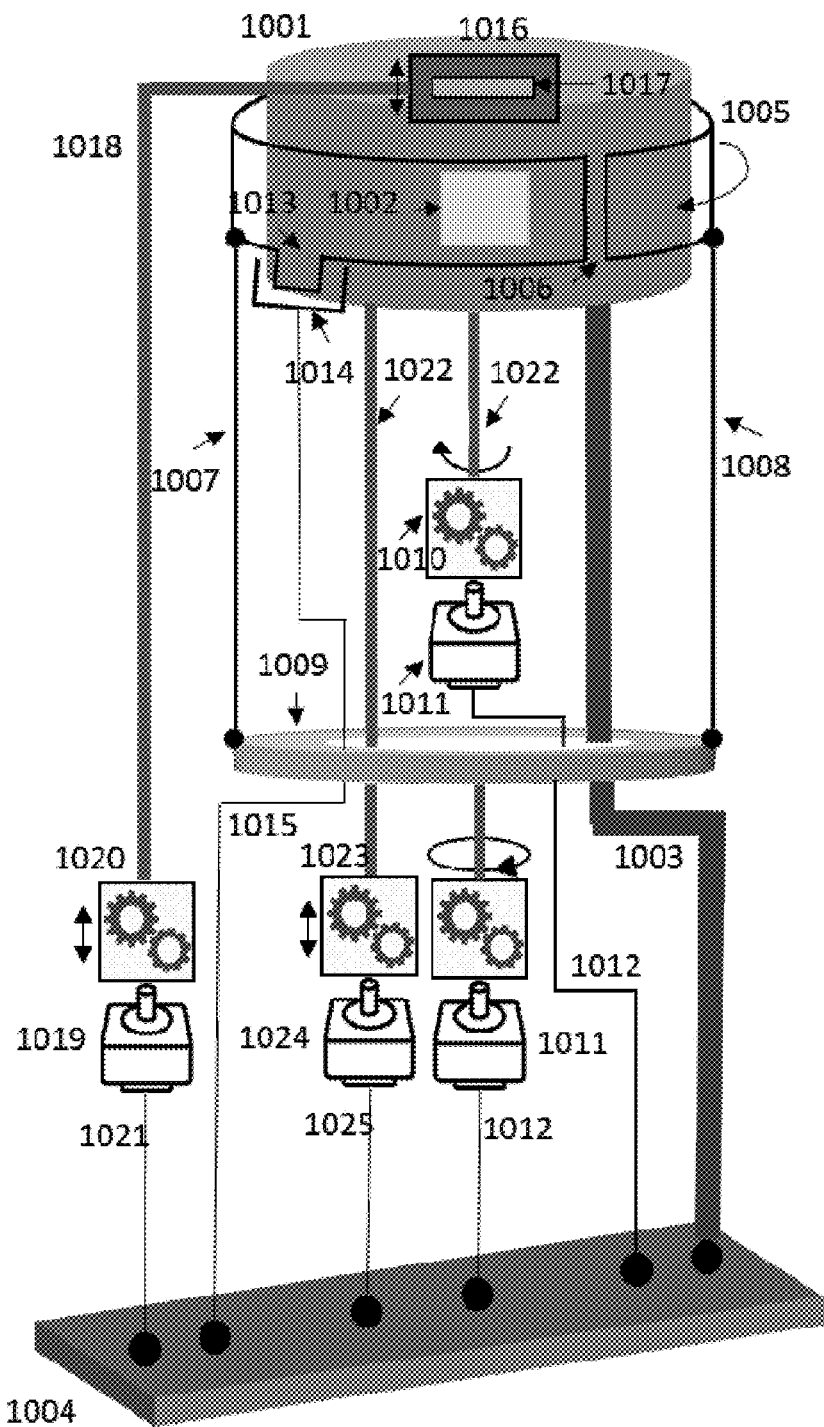
FIG. 10 shows the design of the x-ray generation assembly.

FIG. 10 shows an embodiment of the x-ray production assembly where the produced x-ray photons are collimated according to the position of the x-ray detector assembly. X-rays are generated inside the x-ray tube 1001. X-rays are emitted through a window 1002. The size of the window defines the maximum fan and cone angles. The control and cooling of the x-ray tube are done through a cabling routed through a conduit 1003 to the control unit 1004 where the x-ray generator, control processor and electronics needed to synchronize the imaging sequence and control the system robotics are located. The cooling system may be installed on the x-ray production assembly robotic arm or within the control unit. A spinning collimator ring 1005 is installed on the x-ray production robotic arm. The role of this structure is to allow only a portion of the x-ray beam be projected on an anatomy placed in FOV. A narrow opening 1006 on the ring's structure imposes a limited fan angle coverage on the generated beam. The collimators may be made of a highly x-ray attenuating materials such as lead, lead composite, tin or tungsten. The collimator ring is attached to a hardware links 1007 and 1008 that connect the collimator ring 1005 to a rotary motion actuator system composed of a mounting surface 1009, gear box 1010, a servo motor 1011 and the communication and power cable system that is routed through a conduit 1012 to scanner system's control unit 1004. The rotation of the servo motor's shaft is modulated in the gear box 1010 to provide the rotation speed and the torque necessary for allowing fast spinning of the fan angle collimator ring 1005. A notch 1013 is incorporated into the design of the ring so it can trigger a proximity sensor 1014. Upon detecting the notch within the proximity range, the sensor triggers a pulse that is used to adjust the rotational phase and velocity of the fan angle collimator ring 1005 so that its motion is synchronized with that of the detector panel. The wiring necessary for the proper operation of the proximity sensor is routed through a conduit 1015 to the control unit 1004. In addition to fan angle collimation, the produced x-ray beam at the tube's opening window 1002 undergoes a cone angle collimation to narrow the cone angle coverage of the beam according to the size of the detector panel used. The cone angle collimator is formed from a rectangular slit 1016 with a narrow opening window 3107. X-ray photons that are incident on the collimator 1016 are absorbed by the collimator material. The vertical translation of the cone angle collimator structure is enabled through a robotic link 1018, a servo motor 1019 and a gear box 1020 that converts the rotary movement of the servo motor's shaft to vertical translation. The power and communication wiring between the cone angle collimator structure and the control unit is routed through a conduit 1021 to the scanner system's control unit. To translate the x-ray tube and the collimator structures vertically, the tube is mounted on a robotic link 1022 attached to a gear box 1023 that modulates and converts the rotatory movement of the shaft of a servo motor 1024 to linear motion. The power and communication wiring between the tube translation system and the control is routed through a conduit 1025.

Figure 11:
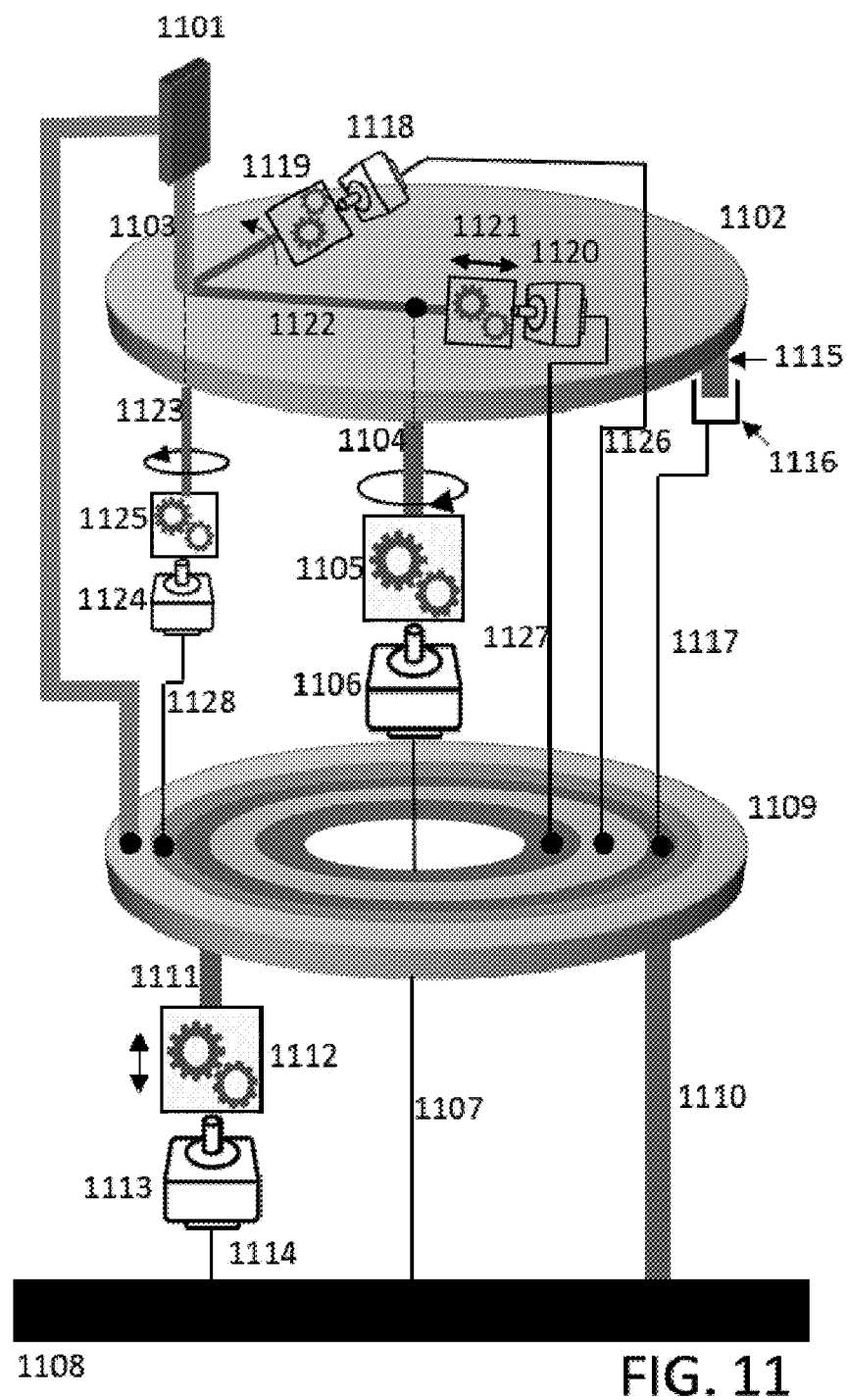
FIG. 11 shows the design of the x-ray detection assembly.

FIG. 11 illustrates an embodiment of the x-ray detection assembly where the x-ray photons that are generated in the x-ray production assembly are captured, converted to digital images and transferred to the reconstruction processor. The detector panel 1101 is mounted on a rotating disk 1102 through a hardware link 1103. An assembly composed of hardware link 1104, a gear box 1105 and a servo motor 1106. The gear box 1105 provides the torque necessary for a rotary motion to the disk 1102. The gear box 1105 is installed on a servo motor 1106 that provides the rotatory motion. The power and communication cables of this servo system are routed through a conduit 1107 to scanner system's control unit 1108. The power and communication link between the components of the disk 1102 and the control unit 1108 is achieved through a multi-channel slip ring 1109. All signal and power lines of the rotating disk 1102 arriving at slip ring 1109 are transferred to the scanner system control unit 1108 through a wiring bundle 1110. A vertical translation of the slip ring and all components attached to it, including the detector ring and the robotics involved, is possible through a hardware link 1111 attaching the slip ring structure to a gear box 1112 that provides the torque necessary for vertical translation of the detection assembly. The gear box is installed on a servo motor 1113 with communication and power wiring routed to the control unit 1108 through a conduit 1114. A hardware notch 1115 is added to the design of the disk to control the phase and rotation speed of the disk 1102. During each rotation of the disk 1102, the position of the notch 1115 is detected by a proximity sensor 1116 and a pulse is triggered and transferred to the scanner rear end 1108 through conduit 1117 and slip ring structure. The pulse train acquired during the rotation of the disk along with the pulse train collected from the x-ray production assembly's collimator ring are used to synchronize the motion of the collimator ring and the detector panel so that all the primary x-ray photons generated by the x-ray production assembly are captured by the detector panel. The detector panel 1101 and its hardware link 1103 are connected to a stepper motor 1118 attached to a gear box 1119. This stepper motor ensures that a perpendicular ray exists in the primary photons of the narrow beam that are captured by detector panel 1101 and are generated in the x-ray production assembly. A robotic structure, composed of a stepper motor 1120 and an attached gear box 1121, may be added to the disk to translate the detector panel along the disk's radius through a hardware link 1122. Another robotic structure, composed of a hardware link 1123, a stepper motor 1124 and an attached gear box 1125, may be added to provide a rotary motion along the surface of the disk 1102. The power and communication wirings between these robotic systems and the slip ring are routed through conduits 1126, 1127, 1128.

Figure 12:
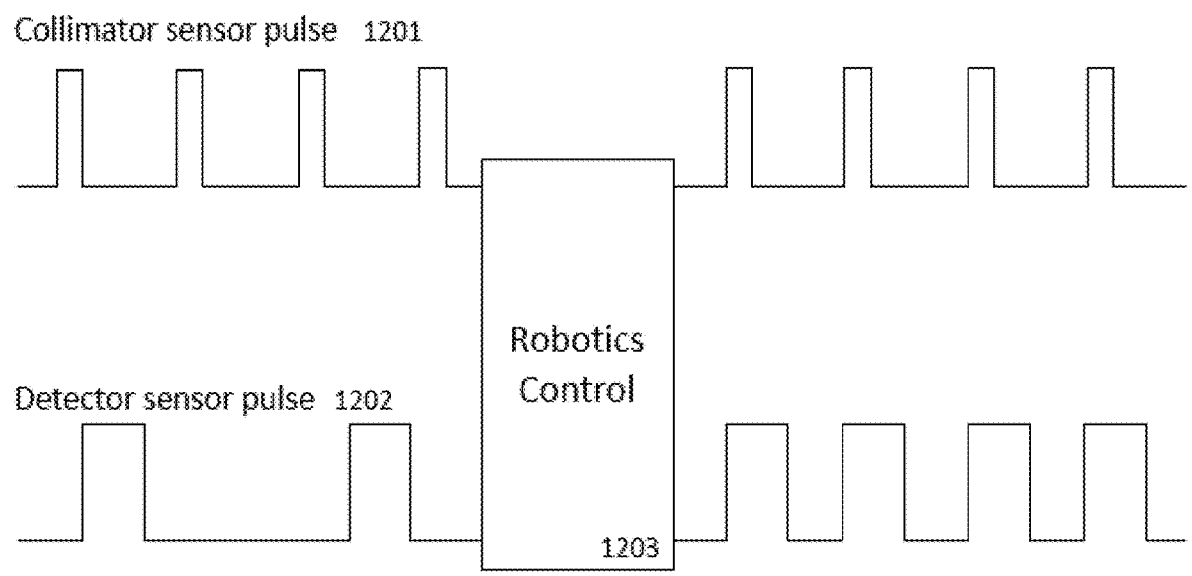
FIG. 12 is a diagram illustrating the synchronization of the robotic motions of the x-ray generation and detection assemblies.

The robotic movements of the x-ray generation and detection assemblies with respect to each other depend on specifications such as the size of the detector panel, the size of the anatomical feature of interest, and the imaging system's geometry. A synchronization between motions of the collimator and detector panel is necessary to ensure capture of all primary x-ray photons by the x-ray generation assembly. FIG. 12 illustrates the basic synchronization mechanism where the signals received from the x-ray generation and detection assemblies' proximity sensors are used by a central control system to synchronize the relative motion of the x-ray collimator and x-ray detector panel. At the start of the initialization phase, which happens before a scan procedure, there is an asynchrony between the circular motions of the collimator and x-ray detection assemblies. Therefore, the pulses arriving from the collimator proximity sensor 1201 and detection assembly's proximity sensor 1202 are entered into a central control system 1203 that adjusts the circular motion speed of the detector assembly so that the pulses are synchronized.

Figure 13:
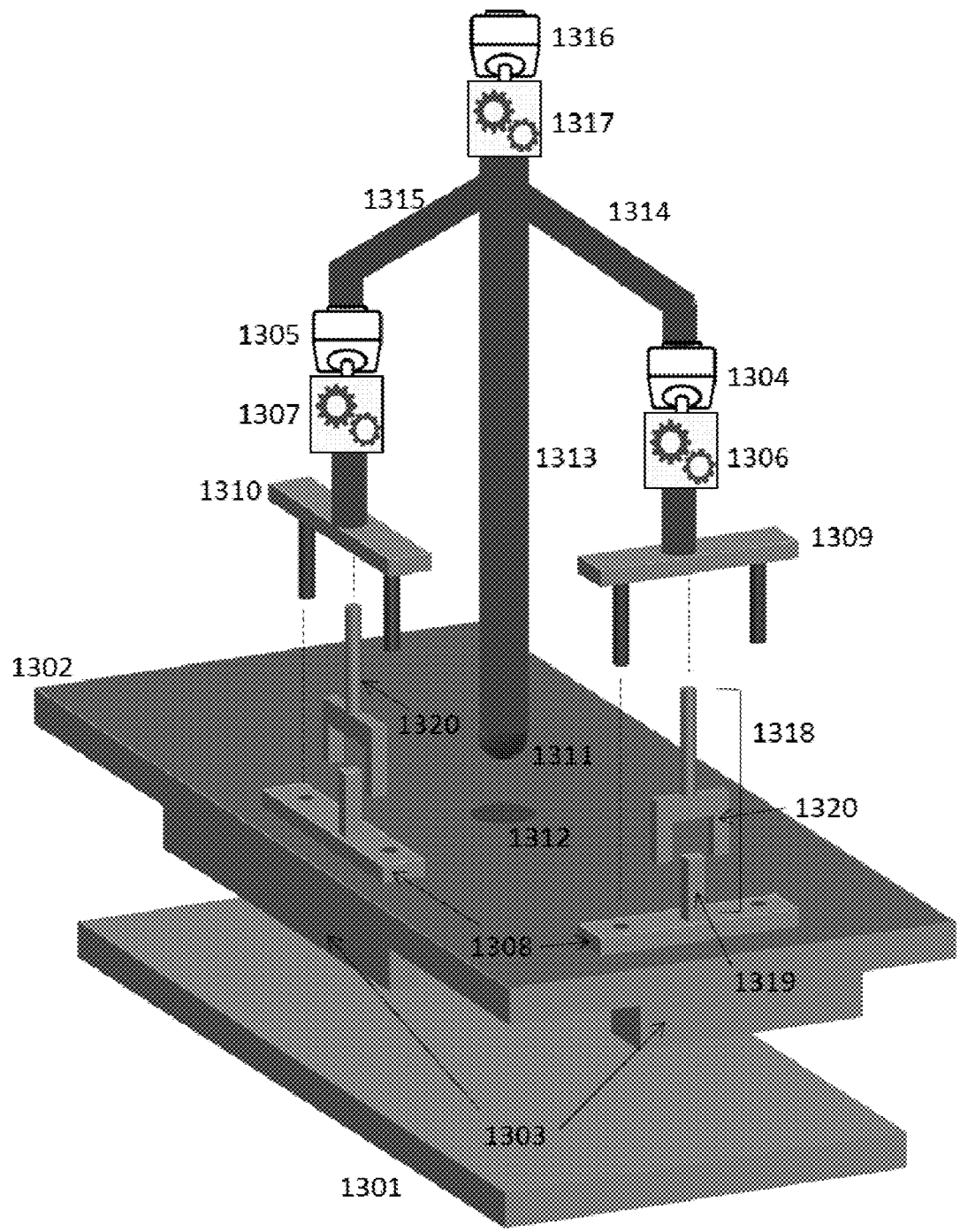
FIG. 13 shows the design of detector tilting mechanism.

The imaging methods described in FIGS. 5J to 5R require tilting the detector panels towards the focal spot to ensure primary beams are incident on the surface of the panel perpendicularly. FIG. 13 illustrates an embodiment of the invention where the motion of a detector panel towards the center of rotation axis (one degree of freedom) and accurate azimuth face positioning (two degrees of freedom) are controlled via a robotic system comprised of a substrate to mount the detector panel, three stepper motors attached to gear boxes to enable motion and convert rotary motion to translation motion, hardware links to link the translating shafts to the substrate and edge sensors to monitor the detector panel's normal and its alignment with primary photons. Each detector panel 1301 is attached to a custom-made hardware substrate 1302 using the clamps 1303 on the periphery of the substrate. In order to change the tilting of the substrate, two computer-controlled actuators articulate the substrate in steps of a few micrometers. Such is the precision needed for a high-resolution CT image acquisition. The actuators 1304, 1305 are paired with gear boxes 1306, 1307 connect to the substrate mounts 1308 through two pointed whiffletrees 1309, 1310. A flex disk is inserted into a hole 1312 on the surface of the substrate to make the azimuthal motion of the detector panel attached to the substrate possible. The flex disk connects to a hardware arm 1313, is conjoined by the two other arms 1314, 1315 and attaches to a stepper motor 1316 via a gear box 1317 that converts the rotary motion of the stepper motor to fine translator steps. To permit a computer software to control the detector panel positioning in real time, positioning feedback is provided by two edge sensors placed perpendicularly with respect to each other. Each sensor 1318 is comprised of a notch 1319 attached to the surface of the substrate and a fork 1320. Placing the notches within the gaps in the forks provides values that combined enable fine tuning the azimuthal positioning of the detector panel. Sensor forks are attached to the whiffletrees using hardware arms 1321.

Figure 14A:
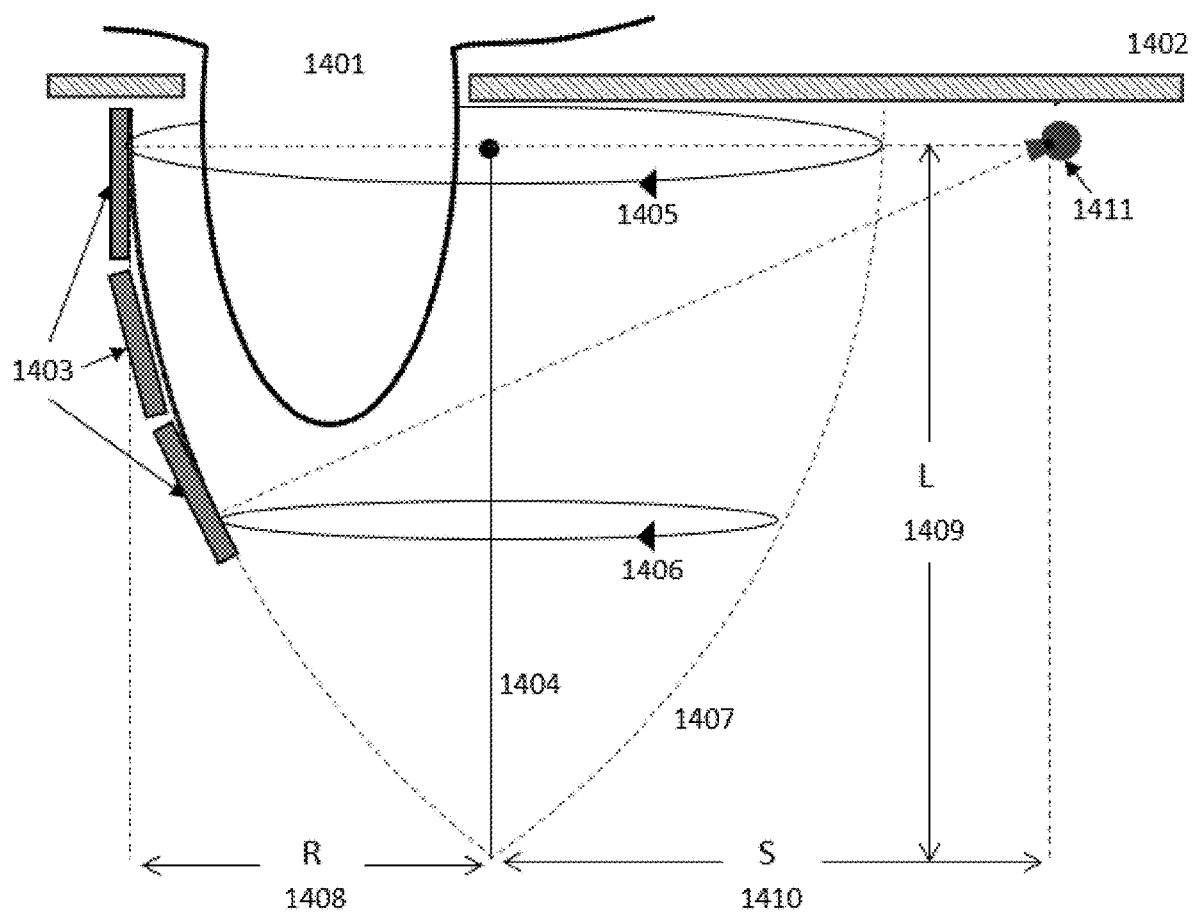
FIGS. 14A and 14B show the method of adjusting the position of the detector panel to conform the shape of a pendent breast.
Figure 14B:
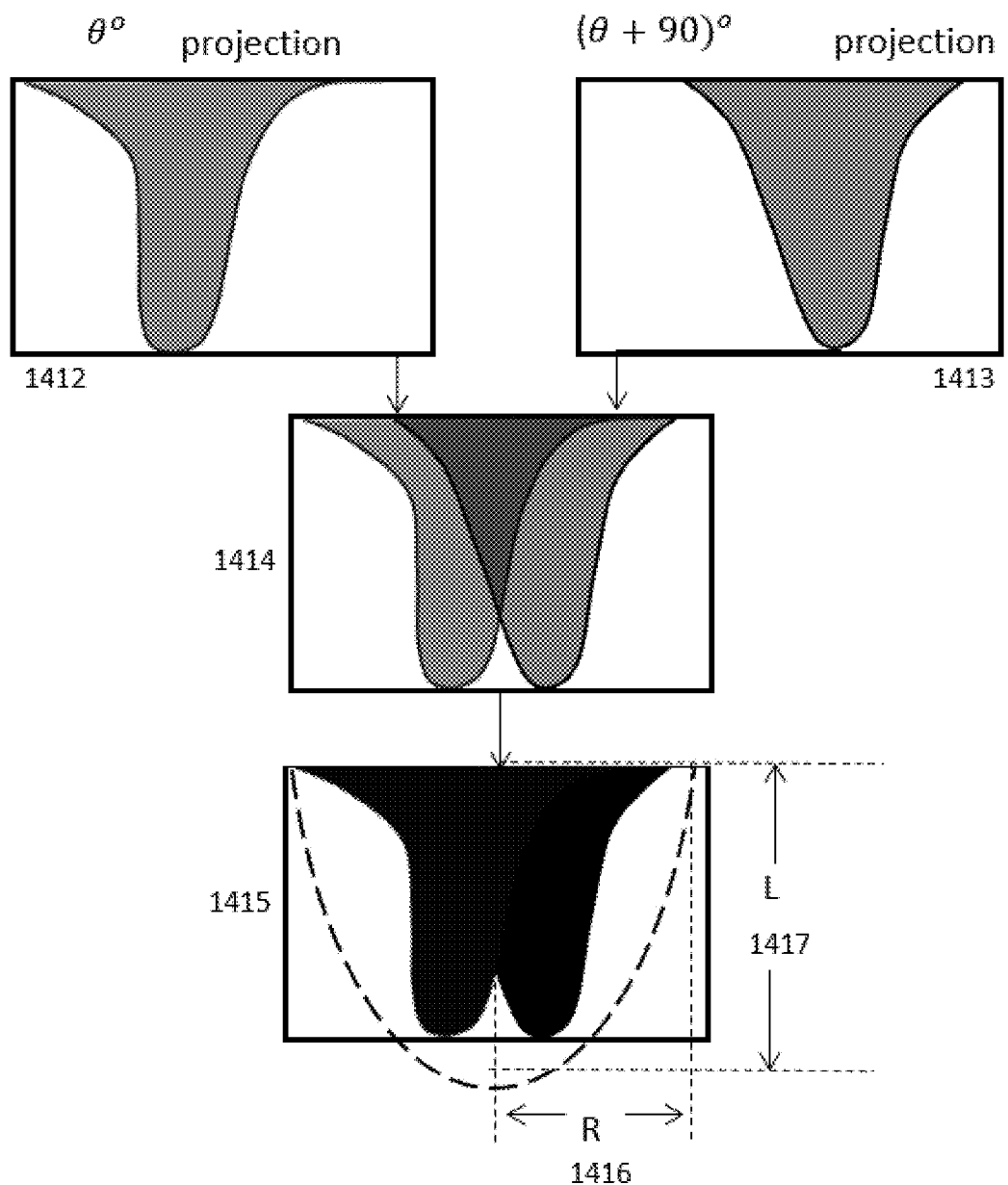

Tilting on the detector panels, enabled through the structured disclosed in FIG. 13, requires information about the size and shape of the anatomy of interest as a prerequisite. For instance, a large diameter extremity positioned in FOV requires a large circular trajectory for detector panels around the anatomy. FIGS. 14A and 14B illustrate an embodiment of the methodology of determining the shape and size of the perimeter of the locus that the detector panel follows to fully acquire an accumulated projection. A breast is shown in FIG. 14A, but any anatomy with an elongation and/or a curvature, such as extremities or head, can employ the same method. A single detector panel in this figure cannot cover the entire diameter and length of the depicted pendent breast. Therefore, a setup such as the one shown in FIGS. 6A-6D is necessary to fully capture the entire breast in an accumulated projection. A typical setup involves positioning a breast 1401 through a hole cut out on the scanner's table top 1402 into the scanner's FOV. The detector assembly's robotic system enables the detector panels 1403 to move around a center of rotation axis 1404 in circular paths. The diameter of the circular path at top coronal plane 1405 is larger than its path at the bottom plane 1406. Detector assembly's movement transverses through periphery of a prolate semi-spheroid dome 1407. The radius R 1408 and the length L 1409 of dome are unknown variables that are dependent on the breast shape and source to isocenter distance, S 1410. Source to isocenter distance is the distance between the focal spot of the x-ray tube 1411 and the axis of rotation of the detector assembly 1404. This embodiment involves a methodology for determining these parameters. First, the detector panels of the detection assembly are aligned vertically with a maximum radius from isocenter axis than can be accommodated by the scanner's FOV. Two orthogonal scout view projections are acquired by placing the x-ray generation assembly at two fixed positions with a 90 degrees angular displacement from each other while acquiring two accumulated projections, named θ degrees 1412 and θ+90° degrees 1413 projections, as displayed in FIG. 14B. Overlapping these projections results in an image 1414 that outlines the overall span of the breast projection shape in different projections during a scan. Applying a simple thresholding on the overlapped image 1414 results in a binary image 1415. An ellipse can be used to fully cover the breast projection in the binary image. The smallest ellipse has a minor 1416 and a major 1417 axes with lengths R and L, respectively. The found values correspond to the parameters that define the shape of the dome 1407 depicted in FIG. 14A. The determined specifications are used for adjusting the position and tilting of each detector panel in preparation for a scan procedure.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A radiologic computed tomography (CT) system for imaging an anatomical target, comprising:
   a) a x-ray generation assembly affixed to a first rotational robotic platform configured to rotate on a first trajectory at a first rotational speed, the x-ray generation assembly comprising:
      i) a x-ray tube; and
      ii) a rotational collimator configured to rotate about an axis of rotation on the first trajectory and perpendicular to the first trajectory,
      the x-ray generation assembly configured to generate a collimated narrow beam of x-ray photons having a fan angle of less than 2 degrees;
   b) a x-ray detection assembly affixed to a second rotational robotic platform configured to rotate on a second trajectory at a second rotational speed, wherein the second trajectory has a smaller radius than the first trajectory, wherein the x-ray detection assembly is robotically independent from the first rotational robotic platform and comprises at least one line detector configured to detect the narrow beam of x-ray photons emitted by the x-ray generation assembly; and
   c) a controller configured to perform at least:
      i) control the first rotational robotic platform to rotate the x-ray generation assembly on the first trajectory at the first rotational speed, and
         control the second rotational robotic platform to rotate the x-ray detection assembly on the second trajectory at the second rotational speed, around the anatomical target; wherein the second rotational speed is higher than the first rotational speed;
      ii) control the rotational collimator to rotate on the first trajectory at the second rotational speed and control targeting of the x-ray generation assembly such that the narrow beam of x-ray photons is incident upon the at least one line detector;
      iii) synchronize the speed and phase of rotation of the rotational collimator and the x-ray detection assembly, wherein during each rotation of the x-ray detection assembly, the rotation of the rotational collimator produces a moving collimated narrow beam sweeping through the entirety of the anatomical target; and
      iv) generate an accumulated projection during each rotation of the x-ray detection assembly based on a spatial union of acquired lines, wherein the accumulated projection conforms to the shape of the anatomical target;
      wherein scattered radiation detected by the at least one line detector is constrained to photons scattered less than 20 degrees from a primary path.

2. The system of claim 1, wherein the x-ray detection assembly comprises a plurality of line detectors.

3. The system of claim 2, wherein each line detector is independently positioned at a cone angle.

4. The system of claim 2, wherein each line detector of the x-ray detection assembly is independently positioned at a tilt angle with respect to a rotational axis of the first trajectory.

5. The system of claim 2, wherein each line detector is independently positioned at a distance from a focal spot of a x-ray source of the x-ray generation assembly.

6. The system of claim 1, wherein the first trajectory is an elliptical trajectory.

7. The system of claim 6, wherein the elliptical trajectory is a helical trajectory or a spiral trajectory.

8. The system of claim 1, wherein the first trajectory is a circular trajectory.

9. The system of claim 8, wherein the circular trajectory is a helical trajectory or a spiral trajectory.

10. The system of claim 1, wherein the second trajectory is an elliptical trajectory.

11. The system of claim 10, wherein the elliptical trajectory is a helical trajectory or a spiral trajectory.

12. The system of claim 1, wherein the second trajectory is a circular trajectory.

13. The system of claim 12, wherein the circular trajectory is a helical trajectory or a spiral trajectory.

14. The system of claim 1, wherein the controller is configured to control the first rotational robotic platform to rotate the x-ray generation assembly on the first trajectory at the first rotational speed and control the second rotational robotic platform to rotate the x-ray detection assembly on the second trajectory at the second rotational speed to capture a plurality of projections, wherein, in the plurality of projections, the first rotational robotic platform rotates around the anatomical target at least 180 degrees and at most 360 degrees, and wherein, in each projection, the second rotational robotic platform rotates around the anatomical target 360 degrees.

15. A method of performing radiologic computed tomography (CT) to image an anatomical target comprising:
   a) generating, by a x-ray generation assembly, a collimated narrow beam of x-ray photons having a fan angle of less than 2 degrees, the x-ray generation assembly affixed to a first rotational robotic platform configured to rotate on a first trajectory at a first rotational speed, the x-ray generation assembly comprising: a x-ray tube and a rotational collimator configured to rotate about an axis of rotation on the first trajectory and perpendicular to the first trajectory;

b) detecting, by a x-ray detection assembly, the narrow beam of x-ray photons, the x-ray detection assembly affixed to a second rotational robotic platform configured to rotate on a second trajectory at a second rotational speed, wherein the second trajectory has a smaller radius than the first trajectory, wherein, the x-ray detection assembly is robotically independent from the first rotational robotic platform and comprises at least one line detector; and c) performing, by a controller unit, at least the following: control the first rotational robotic platform to rotate the x-ray generation assembly on the first trajectory at the first rotational speed; control the second rotational robotic platform to rotate the x-ray detection assembly on the second trajectory at the second rotational speed, wherein the second rotational speed is higher than the first rotational speed; control the rotational collimator to rotate on the first trajectory at the second rotational speed and control targeting of the x-ray generation assembly such that the narrow beam of x-ray photons is incident upon the at least one line detector; synchronize the speed and phase of rotation of the rotational collimator and the x-ray detection assembly, wherein during each rotation of the x-ray detection assembly, the rotation of the rotational collimator produces a moving collimated narrow beam sweeping through the entirety of the anatomical target; and generate an accumulated projection during each rotation of the x-ray detection assembly based on a spatial union of acquired lines acquired in the x-ray detection assembly, wherein the accumulated projection conforms to the shape of the anatomical target;

wherein scattered radiation detected by the at least one line detector is constrained to photons scattered less than 20 degrees from a primary path.

16. The method of claim 15, wherein the x-ray detection assembly comprises a plurality of line detectors.

17. The method of claim 16, further comprising independently positioning each line detector at a cone angle.

18. The method of claim 16, further comprising independently positioning each line detector of the x-ray detection assembly at a tilt angle with respect to a rotational axis of the first trajectory.

19. The method of claim 16, further comprising independently positioning each line detector at a distance from a focal spot of a x-ray source of the x-ray generation assembly.

20. The method of claim 15, wherein the controller unit controls the first rotational robotic platform to rotate the x-ray generation assembly on the first trajectory at the first rotational speed and controls the second rotational robotic platform to rotate the x-ray detection assembly on the second trajectory at the second rotational speed to capture a plurality of projections, wherein, in the plurality of projections, the first rotational robotic platform rotates around the anatomical target at least 180 degrees and at most 360 degrees, and wherein, in each projection, the second rotational robotic platform rotates around the anatomical target 360 degrees.

* * * * *